(12) United States Patent
Li et al.

(10) Patent No.: US 6,881,729 B2
(45) Date of Patent: Apr. 19, 2005

(54) BILE COMPOUND AND METHOD OF CONTROLLING BEHAVIOR OF LAMPREYS THEREWITH

(75) Inventors: Weiming Li, East Lansing, MI (US); Alexander P. Scott, Dorset (GB); Honggao Yan, Okemos, MI (US); Douglas Gage, Okemos, MI (US); Mike J. Siefkes, Richland Center, WI (US); Qin Liu, London (CA); Sangseon Yun, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/207,565

(22) Filed: Jul. 29, 2002

(65) Prior Publication Data

US 2003/0108583 A1 Jun. 12, 2003

Related U.S. Application Data

(60) Provisional application No. 60/308,755, filed on Jul. 30, 2001.

(51) Int. Cl.$^7$ ............................................. A61K 31/575
(52) U.S. Cl. ...................................... 514/179; 514/170
(58) Field of Search ................................. 514/170, 179, 514/182

(56) References Cited

PUBLICATIONS

Bjerselius et al., "Direct behavioral evidence that unique bile acids released by larval sea lamprey (*Petromyzon marinus*) function as a migratory pheromone." Can. J. Fish. Aquat. Sci., vol. 57(3), pp. 557–569, Mar. 2000.*

\* cited by examiner

*Primary Examiner*—Barbara P. Badio
(74) *Attorney, Agent, or Firm*—Ian C. McLeod

(57) ABSTRACT

Novel compounds isolated from the bile of male sea lampreys are described, in particular, 7α,12α,24-trihydroxy-5α-cholan-3-one-24-sulfate and 7α,12α-dihydroxy-5α-cholan-3-one-24-oic acid and an ELISA for detecting the compounds. The bile compounds act as pheromones which attract female sea lampreys in water to the point in the water where the compounds had been introduced. The bile compounds are useful in lamprey population management programs where it is desirable to control the locomotion and distribution of lampreys and in food operations where it enhances the efficiency of catching lampreys for food.

5 Claims, 19 Drawing Sheets

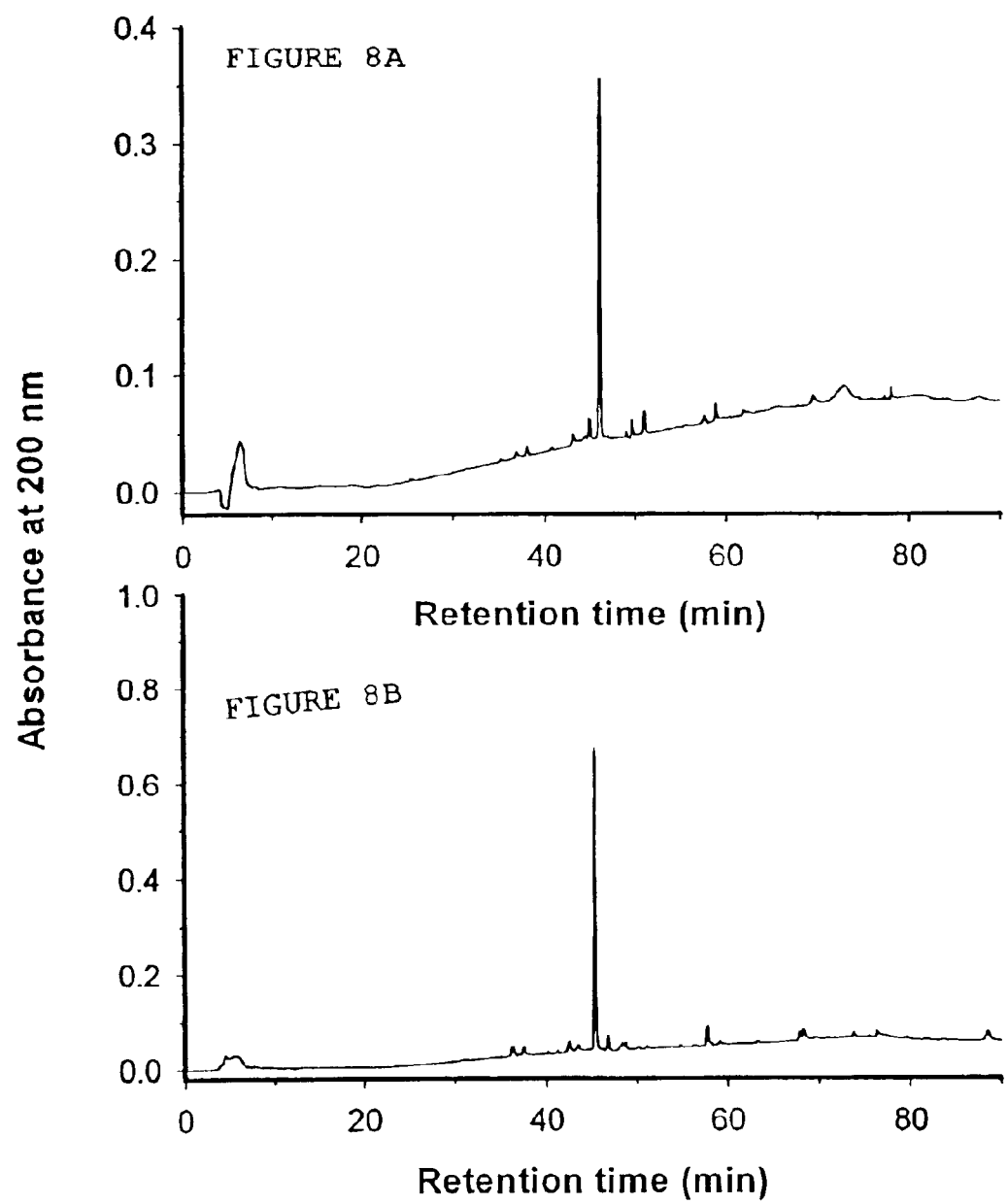

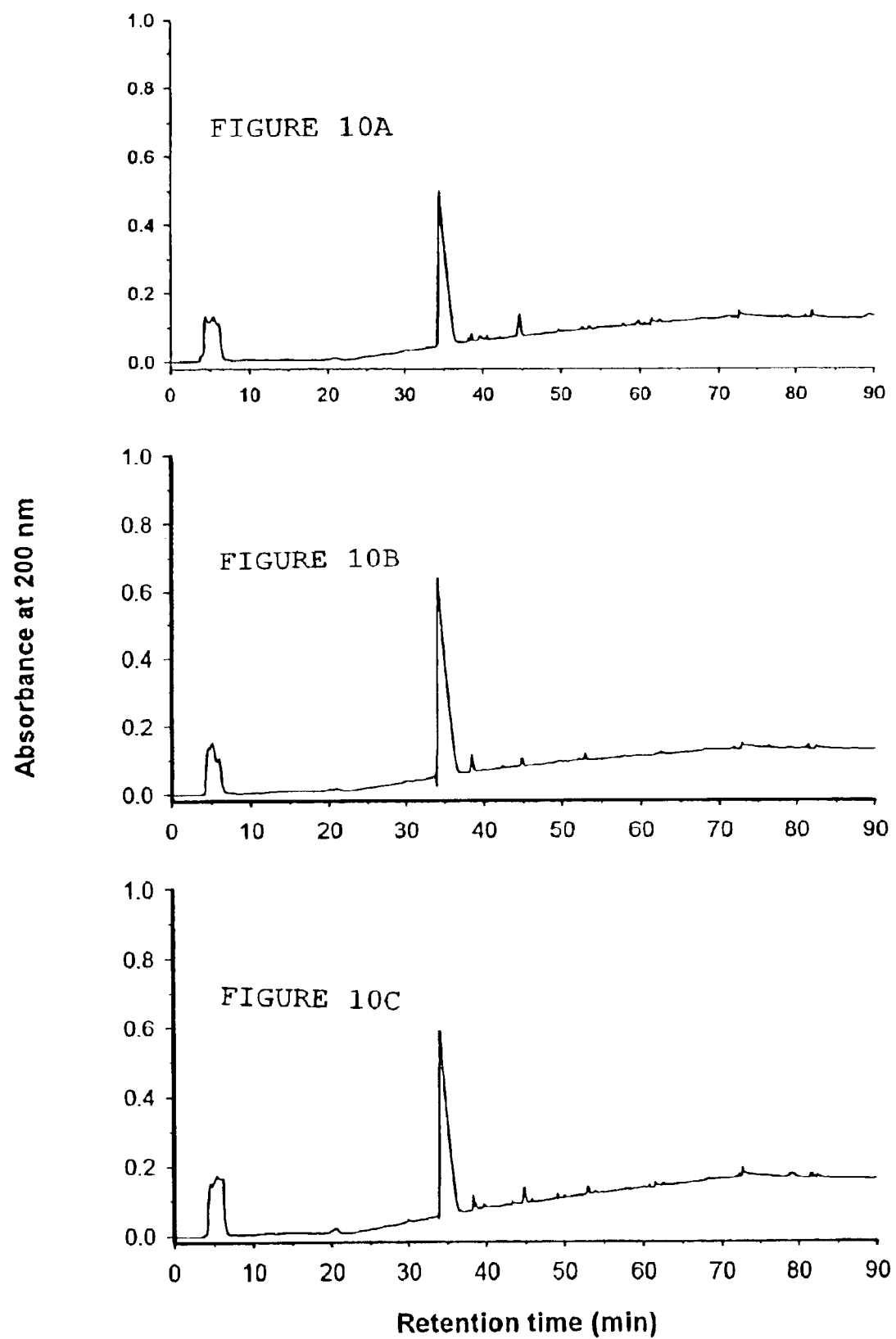

US 6,881,729 B2

BILE COMPOUND AND METHOD OF CONTROLLING BEHAVIOR OF LAMPREYS THEREWITH

CROSS REFERENCE TO RELATED APPLICATION

This application claims priority to U.S. Provisional Application No. 60/308,755, filed Jul. 30, 2001.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to Novel compounds isolated from the bile of male sea lampreys are described, in particular, 7α,12α,24-trihydroxy-5α-cholan-3-one-24-sulfate and 7α,12α-dihydroxy-5α-cholan-3-one-24-oic acid and an ELISA for detecting the compounds. The bile compounds act as pheromones which attract female sea lampreys in water to the point in the water where the compounds had been introduced. The bile compounds are useful in lamprey population management programs where it is desirable to control the locomotion and distribution of lampreys and in food operations where it enhances the efficiency of catching lampreys for food.

(2) Description of Related Art

The sea lamprey, Petromyzon marinus is an ancestral jawless fish and an invasive parasite of fishes in the Great Lakes of North America. It migrates into streams to spawn in spring. The males arrive earlier than the females (Applegate, U.S. Fish Wild. Serv. Spec. Sci. Rep. Fish. Serv. 55: 237 (1950)) and build nests in areas where flow rates are 0.5 to 1.5 m/s (Applegate, U.S. Fish Wild. Serv. Spec. Sci. Rep. Fish. Serv. 55: 237 (1950)); Manion and Hanson, Can. J. Fish. Aquat. Sci. 37: 1635–1640 (1980)). It has long been suspected that the males release a pheromone to guide the females to their nests (Fontaine, Bull. Sco. Oceanogr. Fr. 17: 1681–1687 (1939); Teeter, Can. J. Fish. Aquat. Sci. 37: 2123–2132 (1980)). This type of sex pheromone, capable of inducing spatial orientation of conspecifics "downwind," is well-established in insects (Carde and Minks, Annu. Rev. Entomol. 40: 559–585 (1995)), but not so in vertebrates where identified sex pheromones tend to have a small "active space" (See, Novotny et al., Science 231: 722 (1986); Mason et al., Science 245: 290 (1989); Rasmussen et al., Nature 379: 684 (1996); Dulka et al., Nature 325: 251–253 (1987); Sorensen, et al., Biol. Reprod. 39: 1039–1050 (1988)).

In fish, the known sex pheromones are gonadal steroids or prostaglandins and have been identified from a priori knowledge of their structures (Dulka et al., Nature 325: 251 (1987); Sorensen, et al., Biol. Reprod. 39: 1039 (1988); Stacey and Cardwell, in Recent Advances in Marine Biotechnology, Fingemlan, Nagabhushanam, Thompson, eds. (Oxford-IBH Publ., 1997), pp. 407–454).

There is evidence that sex steroids may function as a male sex pheromone in the sea lamprey. Sexually mature females showed strong preference responses to testosterone at concentrations between 3 and 30 pg/L (Adams et al., J. Chem. Ecol. 13: 387–395 (1987)) and sexually mature male sea lampreys are known to release several immunoreactive sex steroids into the water (Linville et al., Horm. Behav. 21: 105–117 (1987); Adams et al., Olfact. Taste 9: 148–151 (1987)). It has long been hypothesized that hormonal pheromones may be common among aquatic animals (Kittredge et al., Fish Bull. (Natl. Mar. Fish. Serv. U.S.) 69: 337–343 (1971)) and all sex pheromones identified to date in teleosts are sex hormones (Stacey and Cardwell, in Recent Advances in Marine Biotechnology, Nagabhushanam and Thompson (eds.), Oxford-IBH, pp. 407–454 (1997)). Testosterone has been suggested to function as a sex pheromone in the Atlantic salmon, Salmo salar (Moore, Proceed. Fourth Intl. Symp. Reprod. Physiol. Fish, Scott et al. (eds.) U. East Anglia Printing Unit, UK, pp. 241–244 (1991)). The biological significance of the observed preference by female sea lampreys for testosterone, however, needs further examination.

The preference response is over a relatively narrow range of concentrations (roughly $10^{-11}$ to $10^{-10}$ M), which are about 100 times higher than the level of immunoreactive testosterone released by male sea lampreys in behaviorally-active samples (Linville et al., Horm. Behav. 21:105–117 (1987)). Further, immunoreactive testosterone in plasma of sexually mature males is barely measurable (Sower, Fish Physiol. Biochem. 8: 365–374 (1990); Sower et al., Gen. Comp. Endocrinol. 58: 259–269 (1985)). It has been demonstrated that the major androgen in the European river lamprey, Lampetra fluviatilis, is 15β-hydroxytestosterone (Kime and Rafter, In Vitro Gen. Com[. Endocrinol. 44: 69–76 (1981)). If the sea lamprey produces the same androgen, then the differences in immunoreactive testosterone concentrations observed by different workers could be due to differences in the specificity of antibodies against testosterone. This raises the question of whether 15β-hydroxytestosterone, or a metabolite, functions as a pheromone, and if so, is it functionally independent of the bile acid pheromone?

Although sexually mature female lampreys also appear to release a pheromone that attracts male conspecifics (Teeter, Can. J. Fish. Aquat. Sci. 37: 2123–2132 (1980)), the structure of this pheromone has not been identified. The male attracting compound is associated with ovarian fluid of ovulatory females, suggesting that it is synthesized in the ovary and may be related to maturational hormones. The timing of release of the female pheromone is strikingly similar to that of a goldfish female pheromone, prostaglandin F2a (Sorensen et al., Biol. Reprod. 39: 1039–1050 (1988)). However, a direct comparison between lamprey and goldfish is difficult because lampreys are semelparous, having a single spawning period which last for days (Manion and Hanson, Can. J. Fish. Aquat. Sci. 37: 1635–1640 (1980)), whereas, goldfish are iteroparous, with multiple, but short-lived spawning acts, in each spawning season. Consequently, it makes sense that female lamprey pheromone is released over a period of a few days, while female goldfish pheromone is released over a period of hours. Whether biosynthesis of prostaglandins in female sea lampreys can be maintained at a high level over a sustained period in order to function as a pheromone has not been studied. No attempt has been made to fractionate and characterize the structure of the female pheromone in the sea lamprey. It would be interesting to determine whether the female lamprey pheromone is a hormone that is directly associated with ovulation. Maturational hormones have not been studied in the sea lamprey. Plasma levels of immunoreactive progesterone and estradiol are found to increase as the gonads mature (Sower, Fish Physiol. Biochem. 8: 365–374 (1990)). In *L. fluviatilis*, 15α-hydroxy-progesterone has been identified as the main product when ovaries are incubated with progesterone (Kime and Rafter, In Vitro Gen. Comp. Endocrinol. 44: 69–76 (1981)). Whether this is the maturational hormone for female lampreys has yet to be determined.

Because lampreys are an invasive parasite which have had an adverse effect on particular bodies of water such as the Great lakes basin, there has been a great interest in developing means for controlling lamprey populations. For example, in the Great Lakes basin, sea lampreys are effectively controlled to low levels in most spawning streams using trapping of females and lampricides (Smith and Tibble, Can. J. Fish. Aquat. Sci. 37: 1780–1801 (1980)). There are numerous streams in which sea lampreys continue to spawn, but the density is too low to warrant extensive trapping or lampricide treatment. However, these streams, if left untreated, may become major contributors of parasitic phase lampreys entering the lakes to feed. In addition lampricide compounds are not naturally occurring. Therefore, there is a need for compounds which would optimize the mass trapping of adult females, particularly in areas difficult to treat with lampricide or trap by conventional methods. Preferably, the compounds would be environmentally friendly.

SUMMARY OF THE INVENTION

The present invention provides novel compounds isolated from the compounds released from the male sea lampreys are described, in particular, 7α,12α,24-trihydroxy-5α-cholan-3-one-24-sulfate and 7α,12α-dihydroxy-5α-cholan-3-one-24-oic acid and an ELISA for detecting the compounds. The bile compounds act as pheromones which attract female sea lampreys in water to the point in the water where the compounds had been introduced. The bile compounds are useful in lamprey population management programs where it is desirable to control the locomotion and distribution of lampreys and in food operations where it enhances the efficiency of catching lampreys for food.

Therefore, the present invention provides a method for controlling the behavior of female lampreys which comprises introducing an isolated or synthetically produced bile compound into water containing the female lamprey to attract the female lamprey to where the bile compound was introduced.

In a further embodiment of the method, the female lamprey is attracted to a trap in the water or region of the water for sustaining the female lampreys.

The present invention further provides a method for controlling the behavior of a female lamprey in water which comprises introducing a composition which includes 7α,12α,24-trihydroxy-5α-cholan-3-one-24-sulfate and optionally 7α,12α-dihydroxy-5α-cholan-3-one-24-oic acid into the water containing the female lamprey wherein the composition attracts the female lamprey to the region of the water where the composition was introduced.

In a further embodiment of the method, the female lamprey is attracted to a trap in the water or a region of the water for sustaining the lampreys.

In a further still embodiment of the method, the water is a stream in the environment.

The present invention further provides a method for harvesting female lampreys from a body of water which comprises (a) introducing a composition which includes 7α,12α,24-trihydroxy-5α-cholan-3-one-24-sulfate and optionally 7α,12α-dihydroxy-5α-cholan-3-one-24-oic acid into a region of the body of water containing the female lampreys to attract the female lampreys to the region where the composition was introduced; and (b) harvesting the female lampreys from the region of the body of water.

In a further embodiment of the method, the body of water is a stream in the environment.

The present invention further provides a method for controlling the population of lampreys in a body of water which comprises (a) introducing a composition which includes 7α,12α,24-trihydroxy-5α-cholan-3-one-24-sulfate and optionally 7α,12α-dihydroxy-5α-cholan-3-one-24-oic acid into a region of the body of water containing the population of lampreys wherein the composition attracts the female lampreys in the population of lampreys to the region where the composition was introduced; and (b) removing the female lampreys from the region of the body of water wherein removing the female lampreys controls the population of lampreys in the body of water.

In a further embodiment of the method, the body of water is a stream in the environment.

In a further still embodiment of the method, the male lampreys are sterilized after removing from the body of water and then returned to the body of water.

The present invention further provides a composition which comprises (a) 7α,12α,24-trihydroxy-5α-cholan-3-one-24-sulfate; and (b) a carrier.

In a further embodiment of the composition, the carrier is a non-toxic solvent for the 7α,12α,24-trihydroxy-5α-cholan-3-one-24-sulfate.

In a further embodiment, the composition further includes 7α,12α-dihydroxy-5α-cholan-3-one-24-oic acid.

The present invention further provides a compound consisting essentially of 7α,12α,24-trihydroxy-5α-cholan-3-one-24-sulfate which is synthetically prepared or isolated from a lamprey.

In a further embodiment, the compound is in substantially pure form.

The present invention further provides a compound consisting essentially of 7α,12α,24-trihydroxy-5α-cholan-3-one-24-sulfate and 7α,12α-dihydroxy-5α-cholan-3-one-24-oic acid.

The present invention provides a compound with the structure

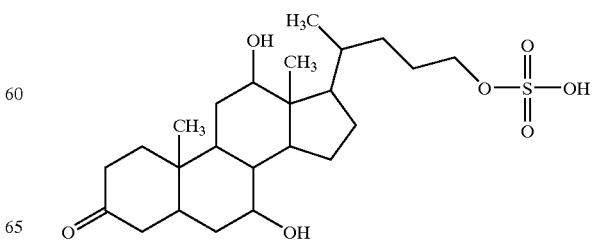

A compound with the structure

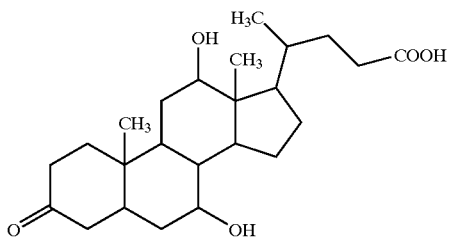

The present invention further provides a kit for detecting 7α,12α,24-trihydroxy-5α-cholan-3-one-24-sulfate and 7α,12α-dihydroxy-5α-cholan-3-one-24-oic acid in a water sample comprising (a) an antibody against the 7α,12α,24-trihydroxy-5α-cholan-3-one-24-sulfate; and (b) a reagent for detecting the antibody bound to the 7α,12α,24-trihydroxy-5α-cholan-3-one-24-sulfate and 7α,12α-dihydroxy-5α-cholan-3-one-24-oic acid.

The present invention further provides a method for detecting 7α,12α,24-trihydroxy-5α-cholan-3-one-24-sulfate and 7α,12α-dihydroxy-5α-cholan-3-one-24-oic acid in a water sample comprising (a) providing a first antibody against the 7α,12α,24-trihydroxy-5α-cholan-3-one-24-sulfate; (b) incubating the first antibody with the water sample for a time sufficient to form an antibody-antigen complex consisting of the antibody or the 7α,12α,24-trihydroxy-5α-cholan-3-one-24-sulfate or the 7α,12α-dihydroxy-5α-cholan-3-one-24-oic acid in the water sample; (c) binding the antibody-antigen complex with a second antibody against the first antibody; and (d) detecting the antigen-antibody complex with a regent.

OBJECTS

Therefore, the object of the present invention is to provide compounds which induce particular behaviors in lampreys.

It is a further object of the present invention to provide compositions which influence the locomotion and distribution of lampreys to human advantage such as population management.

These and other objects of the present invention will become increasingly apparent with reference to the following drawings and preferred embodiments.

DESCRIPTION OF THE DRAWINGS

FIG. 8A shows an HPLC separation (on an analytical column) of a mixture of c. 50 μg of the material in HPLC fractions 58 and 50 μg of 3α-HSD-treated allocholic acid. There is only one peak of absorbance at 200 nm and in exactly the same elution position.

FIG. 8B shows an HPLC separation (on an analytical column) of a mixture of c. 50 μg of the material in HPLC fractions 58 and 50 μg of synthetic 3kACA. There is only one peak of absorbance at 200 nm and in exactly the same elution position.

FIG. 10A shows an HPLC separation (on an analytical column) of 100 μg natural 3kPZS. The sharp UV-absorbing peak at 34/35 min represents 3kPZS.

FIG. 10B shows an HPLC separation (on an analytical column) of 100 μg synthetic 3kPZS. The sharp UV-absorbing peak at 34/35 min represents 3kPZS.

FIG. 10C shows an HPLC separation (on an analytical column) of a mixture of 50 μg natural and 50 μg synthetic 3kPZS. The sharp UV-absorbing peak at 34/35 min represents 3kPZS.

DETAILED DESCRIPTION OF THE INVENTION

Figure 1A:
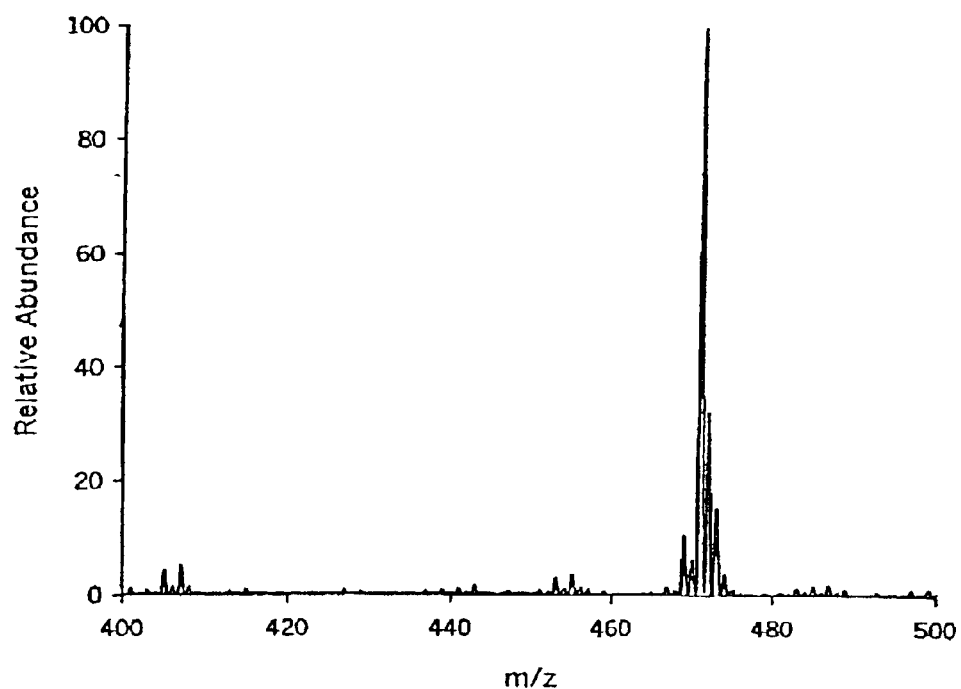
FIG. 1A shows a fast atom bombardment (10 KV) mass spectra of an extract of washings from a spermiating male sea lamprey. Matrix: glycerol.

All patents, patent applications, government publications, government regulations, and literature references cited in this specification are hereby incorporated herein by reference in their entirety. In case of conflict, the present description, including definitions, will control.

Mature male sea lampreys release a potent odorant or pheromone which induces searching and preference behaviors in ovulated female conspecifics. This novel male lamprey pheromone has been identified herein, by activity-directed fractionation and analysis to be 7α,12α,24-trihydroxy-5α-cholan-3-one-24-sulfate (3-keto-petromyzonal sulfate (3kPZS)). This novel male lamprey pheromone has the typical structure of a bile acid, is released only by spermiating males, and attracts ovulated females at sub-nanomolar levels. The structure of the novel male lamprey pheromone is below.

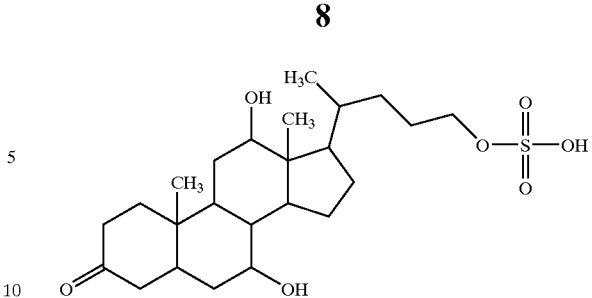

The structure was deduced from chemical analysis of the purified compound and also by comparing its Nuclear Magnetic Resonance (NMR) spectrum with that of synthetic 3-keto-petromyzonol sulfate. The purified 3kPZS is highly stimulatory to olfactory organs of adult females by electro-olfactography (EOG). At sub-nanomolar concentrations, it also induces the same preference and locomotor responses in ovulatory females that are induced by crude washings. This compound is the primary, if not the sole, component of the pheromones released by spermiating males.

The deduced structure of the 3kPZS pheromone is very similar to that petromyzonol sulfate (3α,7α,12α,24-tetrahydroxy-5α-cholan-24-sulfate (PZS), a bile acid released by larval sea lampreys (Haselwood and Tokes, Biochem J. 114: 179–184 (1969)). PZS has recently been shown to function as a pheromone that aids adult sea lampreys in selecting a suitable spawning river during their upstream migration (Li et al., J. Gen. Pysiol. 105: 567–587 (1995); Bjerselius et al., Can. J. Fish. Aquat. Sci. 57: 557–569 (2000)). This indicates that the sea lamprey has evolved an enzyme system that can synthesize two structurally similar, but functionally different, pheromones from the same precursor.

It was further discovered during the course of purification and identification of the 3kPZS pheromone from spermiating, but not non-spermiating males, that at least two other compounds were released into the water. It was discovered by HPLC of water extracts from spermiating males, that there were two fractions that had a stimulatory effect on the olfactory epithelium of adult lampreys. The fraction with the higher potency corresponded to the 3kPZS pheromone, and the fraction with the lower potency to one of the above unidentified compounds. In the course of development of an ELISA for the 3kPZS pheromone (Example 3), it was discovered that both fractions were able to displace enzyme-labeled 3kPZS from the antibody. The novel compound in the fraction was identified as 7α,12α-dihydroxy-5α-cholan-3-one-24-oic acid (3-keto allocholic acid (3kACA)). The structure of the novel 3kACA pheromone is shown below.

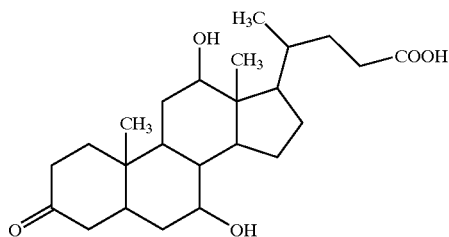

Because the HPLC fractions in which the novel 3kACA pheromone elutes also has electro-olfactogram (EOG) activity, it is likely that the novel 3kACA pheromone enhances or modifies the pheromonal activity of the novel 3kPZS pheromone. This would be similar to 3α,7α,12α,24-tetrahydroxy-5α-cholan-24-sulfate (petromyzonol sulfate (PZS)) and 3α,7α,12α-trihydroxy-5α-cholan-24-oic acid (allocholic acid (ACA)), both of which are released into the water by sea lamprey larvae (Haslewood and Tokes, Biochem J. 114:179–84 (1969); (Li et al., J. Gen. Physiol. 105: 569–87 (1995); Polkinghorne et al., Fish Physiol. Biochem. 24: 15–30 (2001)). Neither PZS nor ACA have been detected in adults (Li et al., J. Gen. Physiol. 105: 569–87 (1995); Polkinghorne et al., Fish Physiol. Biochem. 24: 15–30 (2001)). It has been proposed that PZS and ACA are pheromones which serve to attract adults back to suitable spawning streams based on the facts that the olfactory organs of adults are exquisitely sensitive to PZS and ACA (Li et al., J. Gen. Physiol. 105: 569–87 (1995); Li and Sorenson, J. Comp. Physiol. A. 180: 429–38 (1997)), that larvae release the two compounds at a rate that is sufficient to produce detectable riverine pheromone plumes (Polkinghorne et al., Fish Physiol. Biochem. 24: 15–30 (2001)), and that a mixture of the two compounds elicits positive rheotaxis in migratory adults which are placed in a two-choice chamber Bjerselius et al., Can. J. Fish Aquat. Sci. 57:557–69 (2000)).

Bile acids, which are major products of cholesterol metabolism (Chawla, et al., Cell 103: 1–4 (2000)), are involved in digestion and absorption of lipids in vertebrates (Hoffmann, Arch. Intern. Med. 159: 3647–2658 (1999)). Particular bile acids or derivatives have also been found to be useful as glycoregulatory agents (U.S. Pat. No. 6,060,465 to Miljkovic et al.) or as antifungals (U.S. Pat. No. 5,304,551 to Marples et al.). However, bile acids have not previously been directly implicated in reproduction. Nevertheless, there is some suggestive evidence that bile acids may function as sex pheromones in salmonids.

In lake char, *Salvelinus namaycush*, the composition and concentration of urinary bile acids are sex dependent, with some bile acids that are about 200 times more concentrated in urine of adult males than in urine of juveniles (Zhang, Ph.D. Dissertation, University of Manitoba, Winnipeg, Canada (1996)). These bile acids are potent olfactory stimuli in lake char and, thus have the potential to signal the sex and reproductive state of male char. In rainbow trout, the bile, as well as the urine, of sexually mature females has recently been shown to contain a pheromone which stimulates sex steroid and milt production in males (Vermeirssen and Scott, Gen. Comp. Endocrinol. 101: 180–194 (1996)). The mechanisms for sex dependent biosynthesis and release of bile acids, however, have not been studied. Usually, bile acids are excreted primarily via the intestine, but not via the uro-genital track in fish (Haselwood, Norway Marine Poll. Res. Monitoring Program. No. 1: 24–26 (1983); Sacquat et al., Ann. Biol. Anim. Biochem. A19: 385–391 (1979)).

The 3kPZS pheromone or mixture of the 3kPZS and 3kACA pheromones has several characteristics that make it a particularly useful for exploitation in terms of lamprey population management. First, responses to pheromones are largely instinctual, and thus can be expected from all con-specific individuals that are at a developmental stage which is responsive to the signal. Second, only minute quantities of pheromones are typically needed to elicit specific responses, which are often robust, and which render susceptible animals vulnerable to manipulation with controlled release of the pheromones. Third, pheromones are natural products which because of their species specificity, are not likely to adversely affect individuals of other species that share habitats with the target species, at least at the concentrations typically employed. Fourth and most importantly, for lampreys, which are preponderantly "olfactory animals," chemical cues appear to be essential to completion of the lamprey life cycle. Thus, exploitation of the 3kPZS pheromone provides a powerful means to reduce or increase the lamprey population, or capture lampreys. The usefulness of the 3kPZS pheromone is expected to be synergistically enhanced by including it in a mixture with the novel 3kACA.

Therefore, the present invention provides a novel bile compound isolated from male lampreys which attracts lampreys in water to the point where the compound was introduced into the water. In particular, the present invention provides the compound 7α,12α,24-trihydroxy-5α-cholan-3-one-24-sulfate (3kPZS) as a novel male lamprey pheromone. In particular embodiments, the 3kPZS pheromone is in a carrier, which can be a solvent for the pheromone, or in the case where the pheromone is provided as a solid, the carrier is a solid such as that comprising a water soluble particle such as a powder or the like. Preferably, the carrier is non-toxic. In a further embodiment, the 3kPZS pheromone is provided in a mixture with the novel 3kACA pheromone.

There are numerous ways that the 3kPZS pheromone or mixture of the 3kPZS and 3kACA pheromones can be used. The principle way is to induce lampreys to move to particular locations or in particular directions and to enter traps. Therefore, the 3kPZS pheromone or mixture of the 3kPZS and 3kACA pheromones can be used to lure lampreys to traps, to places where they can not spawn, to places where only sterile males are available, and the like.

Therefore, the present invention further provides a method for controlling the locomotion and distribution of lampreys in bodies of water such as lakes, rivers, streams, and the like as a means for controlling lamprey populations in particular bodies of water. By introducing the 3kPZS pheromone or mixture of the 3kPZS and 3kACA pheromones to a particular point in a body of water, the 3kPZS pheromone or mixture of pheromones will cause female lamprey to migrate to the point where it was introduced. In this manner, spawning females can be collected or directed to particular bodies of water. For example, the 3kPZS pheromone or mixture of 3kPZS and 3kACA pheromones is introduced into particular streams entering a body of water and not other streams entering the body of water. The female lampreys enter the particular streams where they can be caught to be sterilized and released back into the stream or destroyed.

The advantage of the method for controlling lamprey locomotion and distribution as a means for controlling lamprey populations is that it is efficient, it is particularly suitable for use in areas where it is impractical to use pesticides, and unlike most pesticides, it is environmentally friendly. To control the sea lamprey populations in the Great Lakes basin, the prior art methods use pesticides to poison lamprey, or to capture and sterilize the lamprey for later release. By using the 3kPZS or mixture of the 3kPZS and 3kACA pheromones as an attractant, female lampreys can be captured for removal of spawning adults from the body of water or for sterilization of the females with subsequent release back into the body of water.

In addition to providing a means for controlling lamprey populations, the 3kPZS pheromone or mixture of the 3kPZS and 3kACA pheromones is also useful in fishing operations. In some countries, and on Indian reservations, lampreys are considered a delicacy. The 3kPZS or mixture of the 3kPZS and 3kACA pheromones can be used for increasing the efficiency of catching lamprey, and for restoration of reduced or endangered lamprey populations. Female lampreys attracted to the region where the 3kPZS pheromone or mixture of the 3kPZS and 3kACA pheromones has been introduced into the water can be harvested with nets for food consumption or for transfer to areas in need of lampreys. Thus, the present invention further provides a method for controlling the locomotion and distribution of lampreys in bodies of water such as lakes, rivers, streams, and the like as a means for facilitating the harvesting of lampreys for food consumption which would benefit fisheries management agencies, fishermen on Indian reservations and in Europe, Asia, and Australia.

The function of sea lamprey sex pheromones has not been systematically examined. Nonetheless, sea lamprey reproductive biology clearly suggests that pheromones involved in aggregation of opposite sexes, maintenance of spawning pairs or release of spawning behavior would be critical to completion of spawning (Teeter, Can. J. Fish. Aquat. Sci. 37: 2123–2132 (1980)). The 3kPZS appears to function to attract ripe females to spawning nests as shown in Example 1.

Male sea lampreys are often active in the spawning grounds earlier and typically initiate nest construction by excavating a small depression in the gravel. The nest is seldom expanded until a female is present. Therefore, a male pheromone that attracts females to the nest site would be of clear utility. The 3kPZS pheromone fulfills this function. Both laboratory and field observations (Example 1) show that this pheromone triggers searching behavior and upstream movement in ovulatory females, which could bring females to nest sites.

The most significant requirement for nest sites is a steady and unidirectional flow of water (Manion and Hanson, Can. J. Fish. Aquat. Sci. 37: 1635–1640 (1980)). If the water direction or velocity changes, lampreys often leave the nest (Mclain et al., Great Lakes Fishery Comm. Tech. Rep. 10: 48p (1965)). Also, typical nest sites have a flow velocity that ranges from 0.5 to 1.5 m/s (Applegate, Fish. Serv. 55: 237 (1950)). Consequently, a chemical signal released by nesting males will be rapidly flushed down stream. The distance downstream at which a signal can be detected will depend on a variety of factors in addition to flow velocity: the concentration at which the pheromone is released; whether it is released continuously or in a pulsatile fashion; the sensitivity of the responding females. Also, chemical stimuli in rapidly flowing (turbulent) water are distributed downstream as progressively dispersed "scented" packets or eddies, rather than as a continuously decreasing concentration gradient. Packets of relatively high stimulus concentration can therefore be distributed quite far downstream. Ovulatory females, upon detection of this pheromone, will have a higher probability of finding a nesting male if they respond with increased searching effort and swimming against current.

Although the range of concentrations at which the novel male lamprey pheromone is functional has not been determined with particularity, recent behavioral, chemical and electrophysiological experiments (Example 1) all indicate that it functions at very low levels. On average, the 3kPZS pheromone is released at a rate of about 500 $\mu$g/male/hour. Since the water (10 L) collected from pheromone-releasing males in 4 hours is detectable by conspecifics after dilution of $10^6$ times, as determined by EOG experiments (Li, Ph.D. Dissertation, U. Minnesota, St. Paul, Minn. (1994); Berjselius et al., Proceed. Fifth Intl. Symp. Reprod. Physiol. Fish, Thomas and Goetz (eds.), Austin, Tex., pp. 271 (1996)), it is evident that the detection threshold of the 3kPZS pheromone is about $10^{-12}$ molar. The behavioral detection threshold can even be one or two orders of magnitude lower, because 5 males held in a stream with an average discharge of 2.5 m³/s lured ovulatory females to their sites (See Example 1).

Both male and female pheromones are probably involved in maintaining spawning pairs. Sea lampreys are usually monogamous spawners, unless the female to male ratio is very high (Applegate, U.S. Fish Wild. Serv. Spec. Sci. Rep. Fish. Serv. 55: 237 (1950)). The pair, once formed, often stays together until the completion of spawning. Both members of the pair actively participate in nest construction for 1–3 days, and frequently spawn during this period. It would be beneficial for both sexes to release pheromones that promote pair formation and maintenance, and synchronization of spawning.

In an experiment conducted in Ocqueoc River, a major sea lamprey spawning stream in the Great lakes basin (Applegate and Smith, U.S. Fish and Wildlife Ser. Special Sci. Report 61 (1951); Moore and Schleen, Can. J. Fish. Aquat. Sci. 37: 1851–1860 (1980)), it was found that ovulatory females swim to caged spermiating males, often circling in the vicinity until the experiment was terminated (Example 1). It is likely that a pheromone that attracts ovulatory females will also maintain them in the nest. Females would benefit by keeping males in the pair and might also be expected to utilize a sex attractant. In preference tests, males were attracted to both washings and ovarian fluids of ovulatory females (Teeter, Can. J. Fish. Aquat. Sci. 37: 2123–2132 (1980)). One difference between the behavior responses of females and males to sex attractants is that female washings do not appear to promote marked increases in swimming activity in males suggesting the main function of the female pheromone may be in keeping males in the vicinity.

Whether sex pheromones are involved in priming the endocrine system or gonadal development in the sea lamprey has not been studied. In teleost species, both male and female individuals have been found to release pheromones that mainly function to prime the opposite sex (eg., Dulka et al., Nature 325: 251–253 (1987); Van Den Hurk et al., Gen. Comp. Endocrinol. 57: 216–222 (1985)). In pacific herring *Clupea harengus pallasi*, a pheromonal component in the milt has been found to stimulate spawning behavior in both genders (Stacey and Hourston, Can. J. Fish. Aquat. Sci. 39: 489–498 (1982)), indicating the existence of a bisexual primer pheromone. Primer pheromones benefit both genders by promoting paternity and maternity (Zheng et al., J. Exp. Biol. 200: 2833–2840 (1997)). The sea lamprey, in which males and females arrive in the spawning grounds at different times, could certainly benefit from primer pheromones that synchronize gonad development and other aspects of spawning readiness. The limitation on our ability to characterize priming effects of sex pheromones in the sea lamprey, again, is our limited understanding of gonadotropic and steroidal hormones in this species.

The physiological and environmental factors controlling the onset and intensity of sex pheromone communication in sea lampreys have not been clearly defined. Nevertheless, the functionality of lamprey sex pheromones appears to be closely regulated by the reproductive endocrine system. To date, experiments indicate that both the onset of pheromone release and responsiveness to these pheromones are closely correlated with either ovulation or spermiation. In teleosts, the onset, intensity and duration of spermiation and ovulation are closely regulated by the hypothalamus-pituitary gland-gonad axis. In the sea lamprey, and in some other lamprey species, reproduction is under the control of a similar axis (See Sower. Am. Zool. 38: 15–38 (1998)). GnRH play a pivotal role in the regulation of endocrine systems (Sherwood et al., J. Biol. Chem. 261: 4812–4819 (1986); Gazourian et al., Gen. Comp. Endocrinol. 108: 327–339 (1997)) which in turn control spermiation and ovulation.

Water temperature also appears to influence the chemosensory preferences for conspecific cues from the opposite sex in the sea lamprey. Adult sea lampreys, when subjected to a rapid decrease in water temperature, showed a general avoidance of washings from other lampreys, which had previously elicited a preference response (Teeter, Can. J. Fish. Aquat. Sci. 37: 2123–2132 (1980)). Sudden decreases in water temperature of as little as 1° or 2° C. have been reported to result in a decrease in, or even the complete cessation of spawning activity in the sea lamprey (Applegate, U.S. Fish Wild. Serv. Spec. Sci. Rep. Fish. Serv. 55: 237 (1950)) and river lamprey (Hardisty, J. Anim. Ecol. 30: 339–355 (1961)). Whether the loss of preference behavior causes or is the result of a decrease in spawning activity of lampreys subjected to a sudden drop in temperature has not been examined. Other environmental factors that may directly or indirectly influence sex pheromone communication of sea lampreys have not been studied. It is critical to understand how physiological and environmental factors interact to determine the functionality of sex pheromone communication, in particular the timing and intensity of pheromone release and responsiveness, if effective methods are to be developed to disrupt this system.

There are various applications of the 3kPZS pheromone or mixture of the 3kPZS and 3kACA pheromones for lamprey population management. Sex pheromone communication systems have several characteristics that make them a particularly attractive target for exploitation in terms of population management. Responses to sex pheromones are largely instinctual, and thus can be expected from all conspecific individuals that are at a developmental stage that is responsive to the signal. Only minute quantities of pheromones are typically needed to elicit specific responses, which are often robust, rendering animals vulnerable to manipulation with controlled release. Further, pheromones are natural products that are not likely to adversely affect individuals of other species that share habitats with the releasing individuals, at least at the concentrations typically employed. The 3kPZS pheromone appears to have these characteristics. Most importantly, in the sea lamprey, a preponderantly "olfactory animal" (Kleerokoper, in The Biology of Lampreys, Vol. 2, Hardistry and Potter (eds.), pp. 373–404 (1972)), chemical cues appear to be essential to completion of the life cycle. Exploitation of this system using the 3kPZS pheromone or mixture of the 3kPZS and 3kACA pheromones of the present invention provides a powerful means to reduce the lamprey population in particular bodies of water. Thus, the 3kPZS pheromone or mixture of the 3kPZS and 3kACA pheromones is a useful agent for manipulating the sexual behavior of spawning adults in large bodies of water.

Application of sex pheromones in insect pest control has been studied extensively. Most strategies and methods developed for insect management have implications for the use of the novel male lamprey pheromone. The first documented success in direct application of pheromones for insect control was an attraction-annihilation, or mass trapping approach for the spruce bark beetle (Snetsinger and Shelar, Melshimer Entimol. Ser. 32: 12–19 (1982); Chapman, Ann. Rev. Entomol. 45: 261–285 (2000)). By providing a synthetic version of the 3kPZS pheromone or mixture of the 3kPZS and 3kACA pheromones, it is possible to remove a large proportion of females from certain spawning areas. This is feasible because a low concentration of the 3kPZS pheromone has been shown to attract females in their natural habitat (Example 1). Furthermore, the 3kPZS pheromone or mixture of the 3kPZS and 3kACA pheromones can be used to lure females to habitats that are less suitable for spawning or survival of lamprey larvae, or to separate females from males.

One of the most important characteristics of the attraction-annihilation strategy is that its effectiveness is inversely correlated to pest population density and size of target area (Lanier, Behavior-Modifying Chemicals for Pest Management: Applications of Pheromones and Other Attractants, Ridgeway et al. (eds.), Marcel Kekker, New York, pp. 25–46 (1990)). Consequently, this method is most likely to be effective for low-density populations that are immigrant and present in geographically restricted areas. This would be important for the use of the 3kPZS pheromone or mixture of the 3kPZS and 3kACA pheromones.

In the Great Lakes basin, sea lampreys are effectively controlled to low levels in most spawning streams using lampricides (Smith and Tibble, Can. J. Fish. Aquat. Sci. 37: 1780–1801 (1980)). There are numerous streams in which sea lampreys continue to spawn, but the density is too low to warrant extensive trapping or lampricide treatment. However, these streams, if left untreated, may become major contributors of parasitic phase lampreys entering the lakes to feed. Application of the 3kPZS pheromone or mixture of the 3kPZS and 3kACA pheromones to optimize the mass trapping of adult females would provide significant advantages, particularly in areas difficult to treat with lampricide or trap by conventional methods. A constraint on this strategy is within the pheromone communication system itself, because the most serious problem for attracting target individuals is competition from natural sources of attractants. Therefore, optimization of a synthetic copy of the 3kPZS would be important. For oriental fruit flies, lures more attractive than any natural sources of attractant have been developed and applied for fly control (Lanier, Behavior-Modifying Chemicals for Pest Management: Applications of Pheromones and Other Attractants, Ridgeway et al. (eds.), Marcel Kekker, New York, pp. 25–46 (1990)). In theory, this type of lure draws a proportion of the pest regardless of the natural attractants.

Another strategy using the 3kPZS pheromone or mixture of the 3kPZS and 3kACA pheromones is disruption of mating. Although in the broad sense, almost any application of a sex pheromone in the pest control is based on disruption of mating, term is used herein to refer to strategies that do not involve active removal of sea lampreys from spawning streams. Mating disruption has been studied most extensively in moths, resulting in many successful strategies and methods. In their recent review, Carde and Minks (Ann. Rev. Entomol. 40: 559–585 (1995) provided an extensive list of strategies, and commented on the advantages and constraints of these strategies.

In principle, most strategies and practices developed for application of sex pheromones in moth control are applicable in sea lamprey management because the mate finding mechanism of the sea lamprey is strikingly similar to that of moths. In almost all the moth species studied to date, it has been found that the males approach potential mates by flying upwind toward an attractant pheromone released by the females (Carde, Behavior-Modifying Chemicals for Pest Management: Applications of Pheromones and Other Attractants, Ridgeway et al. (eds.), Marcel Kekker, New York, pp. 47–71 (1990)). In the sea lamprey, ovulatory females swim upstream toward a pheromone released by ripe males. Evidently, strategies for the application of the female moth pheromone (Carde and Minks, Ann. Rev. Entomol. 40: 559–585 (1995)), such as generating sensory adaptation or habituation, promoting competition between the natural pheromone and synthetic disrupter, camouflaging the pheromone plumes generated by spermiating males, creating imbalance in sensory inputs, or releasing antagonists, could all potentially be adopted in the application of the 3kPZS pheromone or mixture of the 3kPZS and 3kACA pheromones. Some of these mechanisms could be cooperative and may even be synergistic.

The practical usefulness of this mating disruption strategy, however, needs further study. A major constraint for application of mating disruption is the level of migration by adult sea lampreys which are already on the spawning ground. This method provides no measure to prevent immigration of females from other streams, or from migrating to the target spawning grounds at a much later time—both of which have been documented (Kelso and Gardner, N. Am. J. Fish Manag. 20: 132–141 (2000)). Certain characteristics of this lamprey pheromone communication may also prove to place constraints on the practicality of these methods. It appears that the behavioral responsiveness of females to the novel male lamprey pheromone is quite robust under conditions of continued stimulation; females retained full responsiveness of preference within the 90 minutes they have been continuously exposed to male washings.

The 3kPZS and 3kACA pheromones can produced in quantity by purifying the pheromones following the washing ripe male lampreys as taught in Examples 1 and 2, producing the pheromones in vitro using lamprey liver or pituitary cell cultures derived from 3kPZS and 3kACA producing cells of spermiating lampreys using the protocol that was used by Ma and Collodi (Methods Cell. Sci. 21: 39–46 (1999)) to produce lamprey cell cultures which produce PZS, or chemically synthesizing the pheromones. The chemical synthesis of 7α,12α-dihydroxy-3-oxo-5α-cholanoic acid, which can serve as a precursor for the novel male lamprey pheromone, is disclosed by Iida et al., Chem. Pharm. Bull. 41: 463–465 (1993). In one scheme, the 24-carboxyl group can be converted to a 24-hydroxyl group using $LiAlH_4/H_2O$ and the resulting 24-hydroxyl group then sulfonated with $H_2SO_4$ to produce the novel male lamprey pheromone. Other schemes would be apparent to one skilled in the art. Alternatively, the 3α-OH of synthetically produced PZS, either chemically synthesized or produced in lamprey liver or pituitary cell cultures, can be converted to a 3-keto group using a 3α-hydroxysteroid dehydrogenase as taught in MacDonald (Clin. Biochem. 9: 153 (1976) and in Example 1 to provide the novel male lamprey pheromone. Petromyzonol can be synthesized and converted to the sulfate with sulfotransferase and the 3α-OH converted to the 3α-keto.

The present invention further provides an antibody against 3kPZS. The antibody is highly specific for 3kPZS and 3kACA and has less than 0.2% cross-reactivity with PZ, allocholic acid (ACA), cholic acid (CA), and taurolithocholic acid sulfate. Therefore, the present invention further provides an antigen capture-based immunoassay for detecting 3kPZS and 3kACA in a water sample. The present invention uses a polyclonal or monoclonal antibody to detect whether the 3kPZS and 3kACA are present in a water sample. Both ELISA-based and immunodiffusion-based assays are within the scope of the present invention.

The immunoassay of the present invention is preferably a solid phase immunoassay or derivative thereof. An example of a solid phase immunoassay is an enzyme-linked immunosorbent assay (ELISA) developed by Engvall et al., Immunochem. 8: 871 (1971) and further refined by others such as Ljunggren et al. J. Immunol. Meth. 88: 104 (1987) and Kemeny et al., Immunol. Today 7: 67 (1986). ELISA and its variations are well known in the art, for example, U.S. Pat. No. 5,079,172 to Hari et al. A preferred immunoassay is the ELISA for detecting testosterone, estradiol, and the like using acetylcholinesterase as a tracer which is disclosed in Nash et al., Fish Physiol. Biochem. 22: 355–363 (2000) and described in Example 3 herein.

Other immunoassays such as those disclosed in U.S. Pat. Nos. 5,177,014, 5,219,725, and 5,627,026 to O'Conner et al.; U.S. Pat. No. 5,976,896 to Kumar et al.; U.S. Pat. Nos. 4,939,096 and 4,965,187 to Tonelli; U.S. Pat. No. 5,256,372 to Brooks et al.; U.S. Pat. Nos. 5,166,078 and 5,356,785 to McMahon et al.; U.S. Pat. Nos. 5,726,010, 5,726,013, and 5,750,333 to Clark; U.S. Pat. Nos. 5,518,892, 5,753,456, and 5,620,895 to Naqui et al.; and U.S. Pat. Nos. 5,700,655 and 5,985,594 to Croteau et al. can also be adapted to detect 7α,12α,24-trihydroxy-5α-cholan-3-one-24-sulfate and 7α,12α-dihydroxy-5α-cholan-3-one-24-oic acid using the antibody disclosed in Example 3.

The immunoassay of the present invention can also be provided as a kit comprising an antibody against the 7α,12α,24-trihydroxy-5α-cholan-3-one-24-sulfate; and a reagent for detecting the antibody bound to the 7α,12α,24-trihydroxy-5α-cholan-3-one-24-sulfate and 7α,12α-dihydroxy-5α-cholan-3-one-24-oic acid such as a labeled antibody against the antigen or antibody in the complex or the acetylcholinesterase tracer described in Nash et al. and Example 3. When the antibody is labeled, preferably the label is selected from the group consisting of alkaline phosphatase, horseradish peroxidase, fluorescent compounds, biotin, luminescent compounds, colloidal gold, and magnetic particles. The kit can employ a rapid immunodiffusion-based method such as that disclosed in U.S. Pat. No. 5,620,845 to Gould et al., U.S. Pat. No. 5,559,041 to Kang et al., U.S. Pat. No. 5,656,448 to Kang et al., U.S. Pat. No. 5,728,587 to Kang et al., U.S. Pat. No. 5,695,928 to Stewart et al., U.S. Pat. No. 5,169,789 to Bernstein et al. U.S. Pat. No. 4,486,530 to David et al., and U.S. Pat. No. 4,786,589 to Rounds et al.

The following examples are intended to promote a further understanding of the present invention.

EXAMPLE 1

This example shows isolation and identification of the 3kPZS pheromone. Further shown is its release into the water by the male lamprey and the large active space in which it exerts its effect.

Behavioral tests confirmed that the odor of spermiating males influences the distribution and locomotor activities of ripe females in a two-choice maize as follows. Animals were classified as spermiating males and ovulated females if milt and eggs, respectively, could be expressed by manual pressure, or otherwise as non-spermiating males and pre-ovulatory females, and used as either test subjects or odor donors in a flow through (0.07 m/s) maze (L 4.6 m×W 1.2 m) with plywood bottom, sides, and a partition in the middle which extended 2.4 m from the upstream end, and with plastic meshes blocking fish movement at both the upstream and downstream ends. Odor donors were held above the upstream mesh. Between 0700 and 1700 h, a single test subject was acclimated for 10 min in the maze, and its behavior video recorded for 20 min. Then, 5 lampreys (all of one sex and maturity) were introduced into the mesh chamber on a randomly chosen side, and behavior of test subjects recorded for another 20 min. When washings were used, a spermiating male was held in 10 L of water for four hours and the water introduced into the odor chamber at 75 mL/min. Naïve observers scored videotapes for the total time spent in each side before (Be and Bc) and after (Ae and Ac) odorant introduction. The scores were used to calculate an index of preference: I=(Ae/(Ae+Be))−(Ac/(Ac+Bc)). A similar index was computed for searching behaviors which involved pacing back and forth across the upstream barrier, increased swimming speed, and rapid beating of the tail.

When tested in a two-choice maze, ovulated females (but not males or pre-ovulatory females) spent more time in the compartment scented with washings from spermiating males (Table 1). There was no preference of ovulated females for washings of pre-spermiating males or females. Further, the ovulated females showed dramatic increases in searching behavior in the chamber that contained the odor of the spermiating males (Table 1).

TABLE 1

| Stimuli | No. animals that spent more time on side that was: | | | No. animals that spent more time searching on side that was: | | |
|---|---|---|---|---|---|---|
| | Unscented | Scented | P- | Unscented | Scented | P- |
| SM | 0 | 22 | 0.01 | 0 | 8 | 0.01 |
| NSM | 12 | 12 | NS | 3 | 3 | NS |
| SMW | 3 | 12 | 0.01 | 0 | 7 | 0.01 |
| SME | 3 | 11 | 0.01 | 2 | 7 | 0.05 |
| PP | 0 | 8 | 0.01 | 0 | 6 | 0.03 |
| HW | 2 | 9 | 0.01 | | | |
| TW | 6 | 5 | NS | | | |

Abbreviations: SM, spermiating male; NSM, pre-spermiating male; SMW, washes collected from spermiating males; SME, C-18 SPE extracts of spermiating male washings; PP, purified pheromone; HW, washings collected from head compartment of bisected animals; TW, washings collected from tail compartment of bisected animals. P-values were determined with Wilcox Signed Ranks Test (2-tailed) using indices of preference described in Sorenson et al., Biol. Reprod. 39: 1039 (1988).

A field study at a natural spawning site was conducted in a 65 m segment of the Ocqueoc River, Presque Isle County, Mich. USA, a tributary to Lake Huron—with a barrier to prevent lamprey migration from the lake. The average discharge was 2.3 m$^3$/s. Upstream, an island divided the streams into two channels. Cages (1 m$^3$) of plastic mesh (about 1.5 cm mesh size) containing 5 male lampreys (spermiating or pre-spermiating) were randomly placed in the two channels. A female fitted with an external radio transmitter (Kelso and Gardner, N. Am. J. Fish Manag. 20: 132 (2000)) was acclimated in a cage for two h, released 65 m downstream, and its location recorded every 5 min. Tests were conducted between 0700 and 1700 h in water temperatures ranging from 12 to 24° C. The field study, the ovulated females tagged with radio transmitters and placed 65 m downstream showed a response similar to that observed in the two-choice maize (Table 2)—indicating a large active space for the male pheromone.

TABLE 2

| Test Subject | No. of female lampreys that chose the channel scented with: | | |
|---|---|---|---|
| | SM | NSM | Int. |
| OF | 9 | 0 | 4 |
| NOF | 1 | 2 | 4 |

The test was conducted in the Ocqueoc river. The test subjects: OF, ovulatory female; NOF, preovulatory female. Channels: SM, spermiating male; NSM, pre-spermiating male; Int, intermediate portion of the study site which was downstream of the two scented channels. Lampreys that stayed in the int. were considered to show no preference to either SM or NSM. P-value = 0.02 (Fisher's Exact Test).

To isolate the 3kPZS pheromone, lamprey washings were passed through C-18 solid phase extraction (SPE) cartridges as follows. A lamprey was placed in 10 L of aerated water for 4 h, and removed. The water was drawn through a filter paper (Whatman No.3) and then SPE cartridges (SEP-PAK; Waters Chromatography, Millipore, Milford, Mass., USA; pre-washed with 5 mL methanol, followed by 5 mL distilled water) at a rate of up to 20 mL/min. One L was pumped through each cartridge, which was then washed with 5 mL distilled water and eluted with 5 mL methanol.

Previous electro-olfactogram (EOG) experiments had shown that about 100% of odorant could be extracted by this means (Li, Thesis. University of Minnesota. 184 pp. (1994)). In two-choice maze, ovulated females spent more time and showed increased searching behavior in the side scented with extracts from spermiating males (Table 1).

Figure 1B:
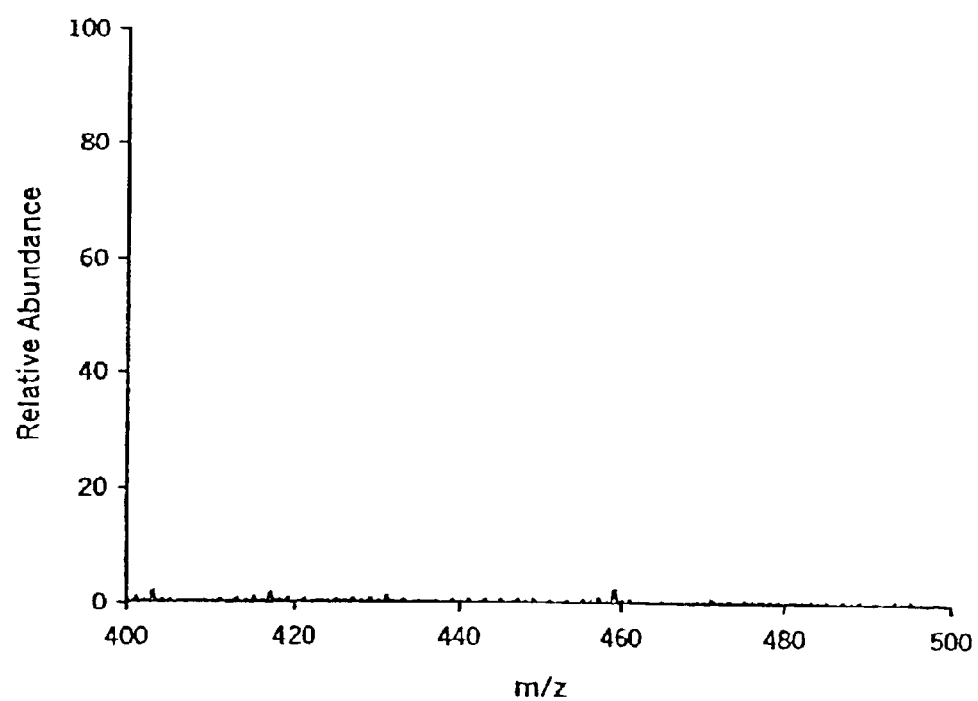
FIG. 1B shows a fast atom bombardment (10 KV) mass spectra of an extract of washings from a pre-spermiating male. Matrix: glycerol.

SPE extracts were subjected to Fast Atom Bombardment Mass Spectrometry (FABMS) and thin-layer chromatography (TLC) to detect the compounds being released by spermiating males, and then to reverse-phase HPLC to isolate them. FABMS identified an abundant ion with an MH$^+$ at m/z 473 in extracts from spermiating males. In the negative mode, a corresponding strong [M−H]$^-$ ion at m/z 471 was observed, suggesting the presence of an acidic moiety in the molecule (FIG. 1A). Tandem analysis of this peak showed it lost 98 mass units, suggesting that the compound was phosphorylated or sulfated. Similar ions were not present in detectable amounts in extracts from pre-spermiating males (FIG. 1B), or females (data not shown).

Figure 2A:
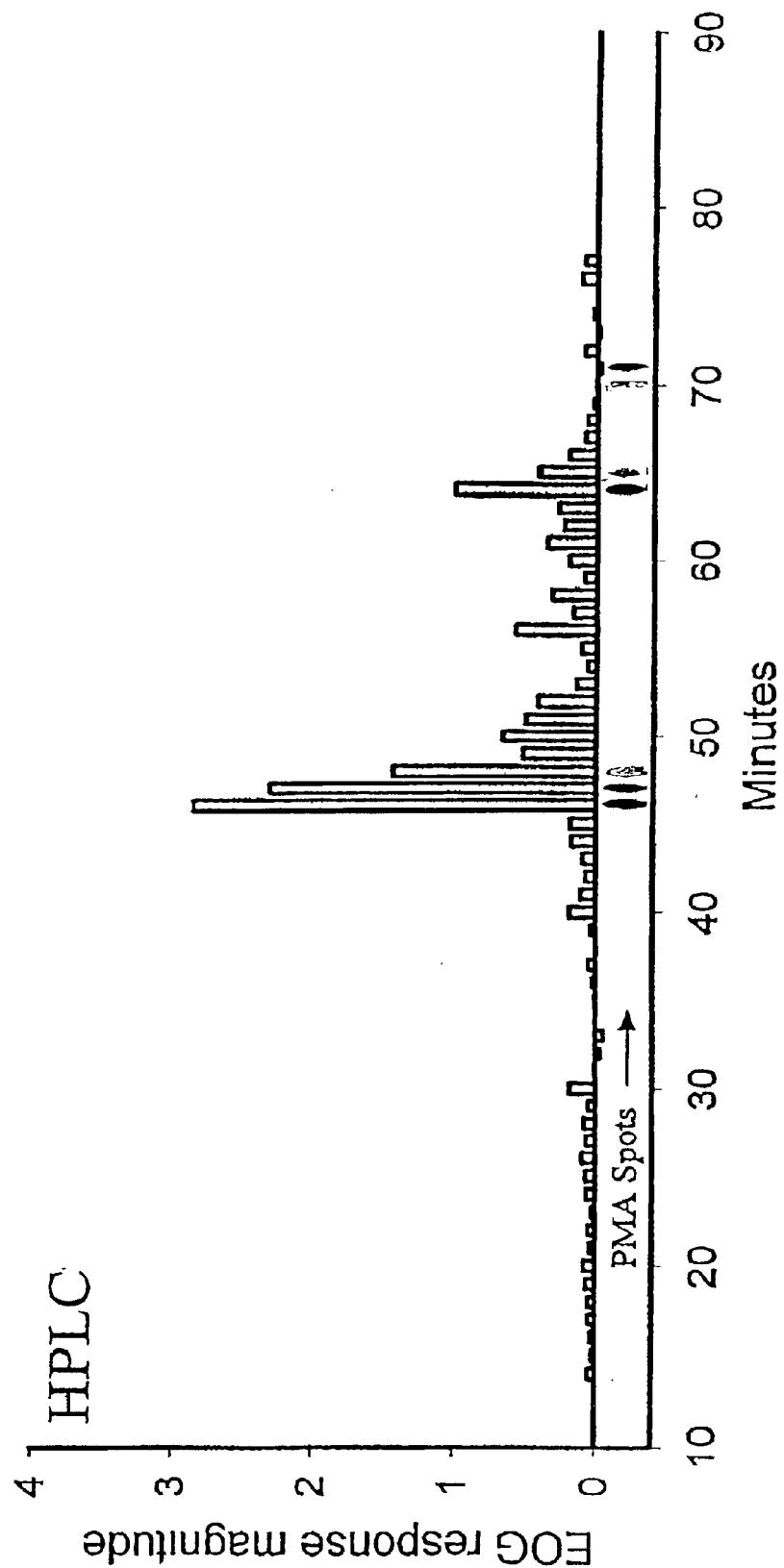
FIG. 2A shows the electro-olfactographic (EOG) potency of fractions derived from reverse-phase HPLC separation of water extracted from five spermiating male lampreys. The spots produced by staining of 5 μL of each fraction with phosphomolybdic acid (PMA) are shown just below the ordinate.
Figure 2B:
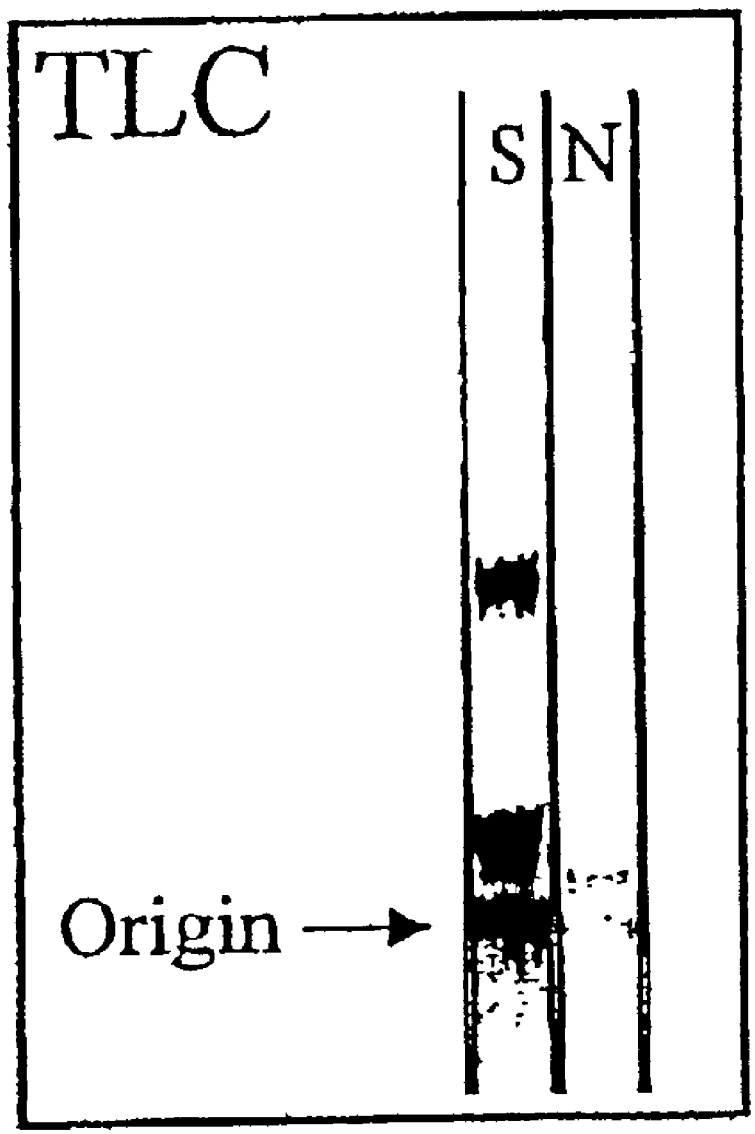
FIG. 2B shows a thin-layer chromatography (TLC) of equal amounts of extract from spermiating (S) and pre-spermiating (N) male lampreys; followed by staining with PMA. The three TLC bands had the following correspondence to the HPLC fractions: origin=46/47; slow-moving band=71; fast-moving band=64. Note well, the staining method is not quantitative; thus the relative size of the TLC bands is not a true reflection of their relative abundance.

TLC of extracts (17) displayed a relatively large amount of a few major compounds in spermiating, as opposed to pre-spermiating, male washings (FIG. 2B). For the TLC, samples were loaded in 50 µL ethanol on silica gel plates (Whatman type LK6DF) which were developed with chloroform:methanol (50:6; v/v) for 45 min., sprayed with 5° phosphomolybdic acid (PBA) in methanol, placed on a hot-plate at 100° C. for 3 to 5 min to develop the color, and photocopied. The material separated into three bands on TLC; the one at the origin being established, by dilution, as the most abundant. The HPLC (Scott et al., Gen. Camp. Endocrinal. 105: 62 (1997)) fractions eluting at 46 and 47 minutes contained a 472 Dalton molecule by FABMS analyses, stained strongly by PBA when spotted on TLC plates, remained at the origin when run on TLC, and had the highest olfactory potency by EOG (FIG. 2A) (Sorensen and Gallaher, J. Gen. Physiol. 105: 567 (1995)). Fractions 64 and 71 are unidentified.

The chemical structure of the 472 Dalton molecule was determined by magnetic resonance spectrometry. The samples were dissolved in perdeuterated methanol or dimethyl sulfoxide (DMS) and subjected to a Varian INOVA 600 spectrometer at 25° C. for two-dimensional homonuclear $^1$H COSY and TOCSY spectra, and heteronuclear $^1$H-$^{13}$C HSQC, HSQC-TOCSY, and HMBC spectra. The one-dimensional $^{13}$C spectrum was acquired on a Varian VXR 500 spectrometer. Standard pulse sequences were used. Suitable window functions were applied to the time domain data before Fourier transformation for resolution or sensitivity enhancement. Both $^1$H and $^{13}$C chemical shifts were referenced to the solvent resonances.

Figure 3A:
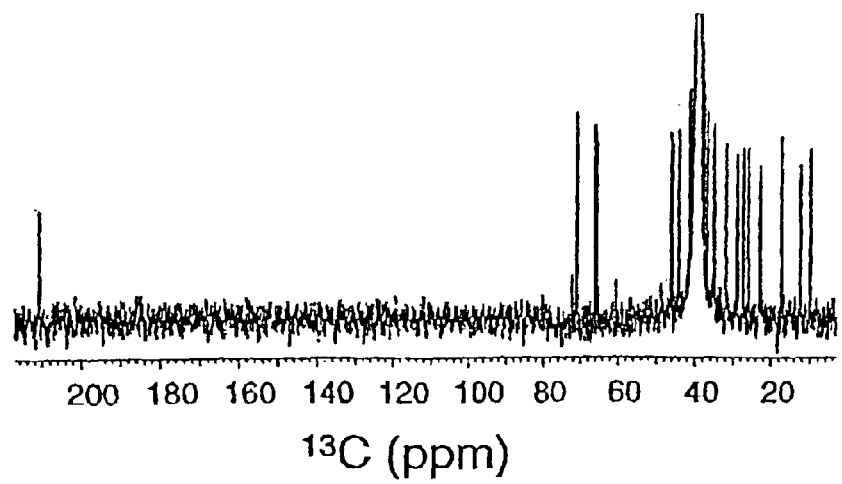
FIG. 3A shows a one-dimensional $^{13}$C spectrum of the isolated male 3kPZS pheromone.

The one dimensional $^{13}$C spectrum (FIG. 3A) showed one peak at 210.9 ppm and no other peaks above 80 ppm, suggesting the presence of a carbonyl group and absence of double bonds between carbon atoms. The $^1$H-$^{13}$C HSQC (FIG. 3B) showed three intense cross peaks characteristic of CH$_3$ groups. Two of them were singlet peaks, suggesting they were bonded to quaternary carbons. CH and CH$_2$ groups were distinguished by $^{13}$C-editing. The cross peaks with $^1$H chemical shifts >3.0 ppm and $^{13}$C chemical shifts >60 ppm were assigned to $CH_2$ or CH groups linked to an oxygen via a single bond. These chemical groups were then linked together via through bond correlations obtained from two-dimensional $^1$H-$^1$H COSY and TOCSY and $^1$H-$^{13}$C HSQC-TOCSY and HMBC spectra. The stereochemistry of 7-H and 12-H was determined on the basis of their narrow multiplets (<10 Hz), and that of 5-H on the basis of the chemical shift of C-19 (9.7 ppm) (Setchell et al., in The Bile Acids, Plenum Press, N.Y., (1988); Haslewood and Tokes, Biochem. J. 114: 179 (1969)). The formula based on this structure, $C_{24}H_{40}O_7S$, was confirmed by an exact mass measurement (MH$^+$ calculated, 473.2573; observed, 473.2578; error 1.1 ppm), indicating the compound contained a sulfate rather than a phosphate group. We concluded that the structure of the novel male lamprey pheromone was 7α,12α,24-trihydroxy-5α-cholan-3-one-24-sulfate.

The deduced structure differs from that of petromyzonol sulfate (3α,7α,12α,24-tetrahydroxy-5α-cholan-3-24-sulfate; PS) by its 3-keto group, as opposed to the 3α-hydroxyl group of PS. PS is a lamprey larvae bile acid (Sorensen and Gallaher, J. Gen. Physiol. 105: 567 (1995); Haslewood and Tokes, Biochem. J. 114: 179 (1969)) and a component of a pheromone which influences behaviors of migrating, but not ripe, adults (Sorensen and Gallaher, J. Gen. Physiol. 105: 567 (1995); Bjerselius et al., Can. J. Fish. Aquat. Sci. 57: 557 (2000)).

We converted the 3α-OH of synthetic PS into a 3-keto group according to MacDonald (Clin. Biochem. 9: 153 (1976). Briefly, the following mixture was shaken at 37° C. for 5 h: 10 mg of petromyzonol sulfate (Toronto Research Chemicals, Inc.) in 1 mL methanol; 40 mg of β-nicotinamide adenine dinucleotide (NAD) in 50 mL 0.05M CAPS buffer at pH 10.8; and 10 units of 3α-hydroxysteroid dehydrogenase (Sigma Chemical Co.) in 100 μL 0.1 M sodium phosphate buffer at pH 7.6. A further 20 mg NAD and 10 units of enzyme were added at 1 h. The products of the reaction were extracted with SPE cartridges and purified by HPLC (Scott et al., Gen. Camp. Endocrinal. 105: 62 (1997)). The $^1$H-$^{13}$C HSQC of the converted PS was acquired as above. The chemical shifts and intensity of cross peaks were virtually identical between the converted compound and the purified male pheromone (FIG. 3B), suggesting that both molecules had an identical chemical structure and similar purity. Further, these two compounds co-migrated on TLC, co-eluted on HPLC, and showed the same fragmentation patterns under FABMS.

Figure 3B:
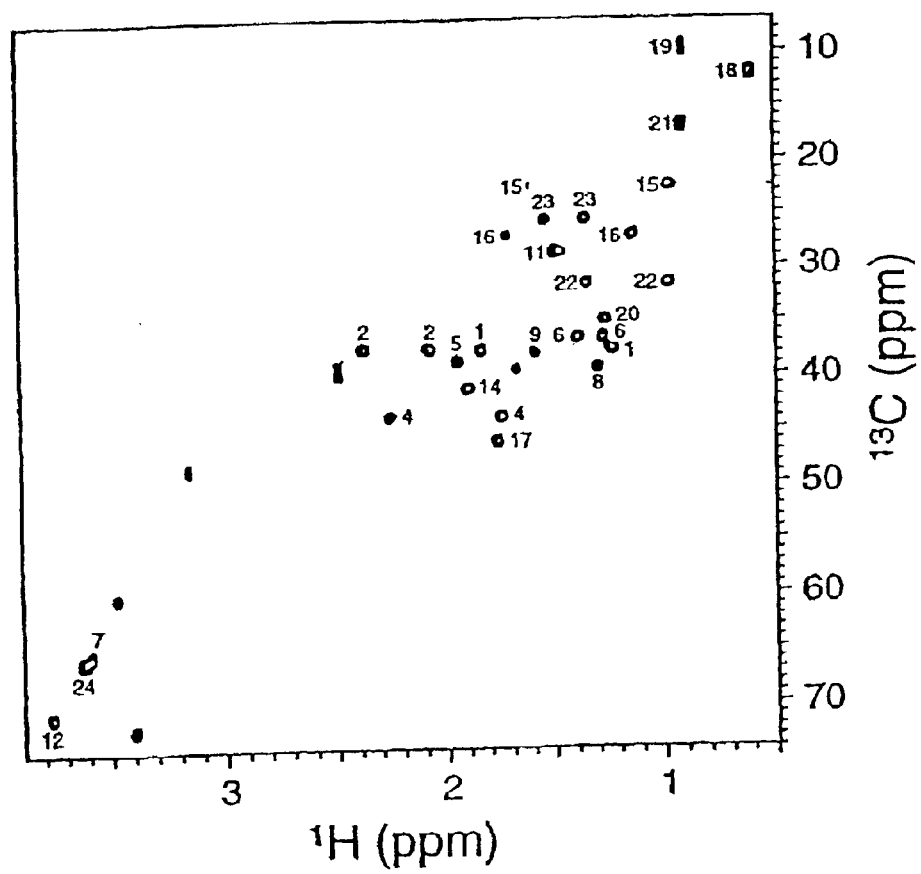
FIG. 3B shows a two-dimensional $^{1}$H-$^{13}$C HSQC spectra of the isolated (red) and synthetic (green) 3kPZS pheromone. The unlabeled cross peaks in the $^{1}$H-$^{13}$C HSQC spectrum are due to impurities of the solvent.

We confirmed that the purified compound (which showed an identical $^1$H-$^{13}$C HSQC to the synthetic compound; FIG. 3B) replicated the pheromonal activity of washings of spermiating males. Approximately 30 mg pheromone was isolated from 4 h washings of approximately 30 spermiating males, suggesting a rate of release of about 250 μg/male/h. From this we estimated that in the two-choice maze experiments with live males, the pheromone reached a concentration between 0.1 and 0.2 ηM. Therefore, the converted PS was tested in the two-choice maze at a final concentration of 0.17 ηM. Ovulated females spent a longer time and showed increased searching behavior in the scented side (Table 1).

Figure 4:
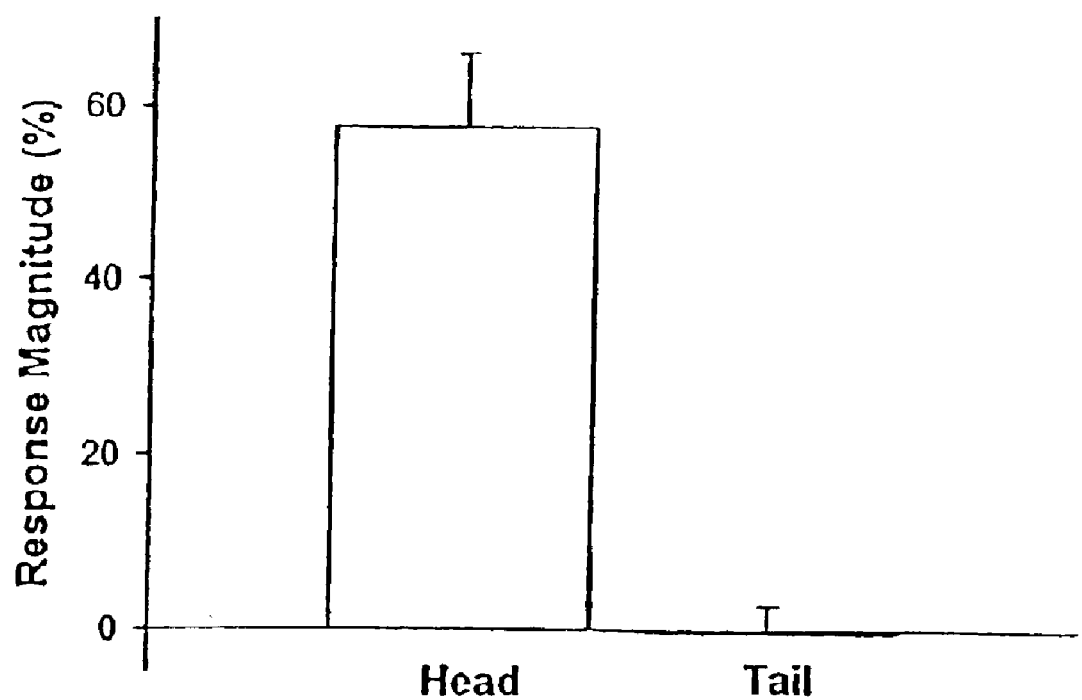
FIG. 4 shows the olfactory potency of washings (10,000 times dilution) collected from the anterior (head) and posterior portions (tail) of bisected spermiating male sea lampreys (n=5). The response magnitude is expressed as the percentage of responses to $10^{-5}$ M L-arginine, the standard odorant. Vertical bars, one standard deviation.

In order to determine the site of release of the pheromone, we tested washings from bisected (Vermeirssen and Scott, Gen. Comp. Endocrinal. 101: 180 (1996)) male lampreys. Only the water from the head region induced an EOG response at 10,000 times dilution (FIG. 4), was attractive to ovulated females (Table 1), and, by FABMS, contained the [M–H]$^-$ ion at m/z 471 (data not shown).

We conclude that ripe male lampreys release a large amount of 7α,12α,24-trihydroxy-5α-cholan-3-one-24-sulfate, most likely via the gills, to signal the location of their nests to ovulated females at a long distance downstream. The selection pressure favoring the evolution of a bile acid derivative, rather than a steroid or prostaglandin, as a sex attractant may have been the necessity to cover a large active space. Bile acids, in particular sulfated ones, are more water-soluble and can be produced in larger quantities than steroids. A spermiating male lamprey (ca. 250 g) releases sufficient quantities of this pheromone in 4 h to be detectable by females when diluted in $10^7$ L of water (Li, Thesis. University of Minnesota. 184 pp. (1994); Bjerselius et al., Proc. Fifth Intl. Symp. Reprod. Physiol. Fish, Austin, Tex., Thomas and Goetz, eds., pp. 271 (1995)). This volume is about $10^5$ times greater than that (130 L) for the main gonadal (steroid) pheromone released by a 25 g female goldfish (Scott and Sorensen, Gen. Comp. Endocrinal. 96: 309 (1994)).

Preliminary tests indicate that 7α,12α,24-trihydroxy-5α-cholan-3-one-24-sulfate is present in the liver of spermiating males (data not shown), suggesting that this is where it is synthesized. It is unlikely that this bile acid is needed for lipid digestion since adult lampreys do not feed, nor do they have bile ducts or gall bladders (Yamamoto et al., Hepatol. 6: 54 (1986)). Its delivery to the gills must be via the bloodstream. Because the hepatic portal system carries blood directly to the heart—and because all the blood from the heart goes through the gills—its excretion is potentially very efficient. However, at the level of the gills, there would appear to be a problem. In elasmobranchs and teleosts (Vermeirssen and Scott, Gen. Comp. Endocrinal. 101: 180 (1996); Maren et al., Comp. Biochem. Physiol. 26: 853 (1968)), the passive transfer of sulfated compounds across gills is negligible.

How have lampreys overcome this problem? Interestingly, concomitant with spermiation, profuse glandular cells with secretory papillae (that have actually been proposed to excrete "sex substances") appear in the gills of spermiating males (Pickering, Cell Tiss. Res. 180: 1 (1977)). Females do not develop these cells at any stage. It is most likely that these cells are responsible for the active excretion of the identified pheromone. If so, this suggests that male lampreys are "active signalers" rather than the females being "chemical spies," the current leading hypothesis concerning the evolution of fish sex pheromones (Stacey and Cardwell, in Recent Advances in Marine Biotechnology, Fingemlan, Nagabhushanam, Thompson, eds. (Oxford-IBH Publ., 1997), pp. 407–454; Scott and Sorensen, Gen. Comp. Endocrinal. 96: 309 (1994)).

As shown in this example, the 3kPZS pheromone influences distribution and oriented locomotion of female lampreys in their natural habitat (Table 2). Interference with this pheromone system offers an attractive target for selective and environmentally benign control of the sea lamprey, whose invasion of the Great Lakes represents arguably the worst ecological disaster ever to befall a large watershed (Smith and Tibbles, Can. J. Fish. Aquat. Sci. 37: 1780 (1980)).

EXAMPLE 2

This example shows the results of chemical and chromatographic studies which establish the presence of 3-keto allocholic acid (3kACA) in water extracts from spermiating male sea lamprey, *Petromyzon marinus*. This is the second compound to be isolated and identified from these extracts.

The first was 3-keto petromyzonol sulfate (3kPZS), which was shown in Example 1 to act as strong pheromonal attractant for ovulated females. Some new characterization data on 3kPZS (utilizing an only recently available synthetic preparation of the compound) is included in this example. This example also shows that a mixture of 3kACA and 3kPZS might be a more potent pheromonal attractant than either compound alone.

Materials and Methods

Chemicals

Synthetic 7α,12α,24-trihydroxy-5α-cholan-3-one (3-keto petromyzonol; 3kPZ), PZS, 5-cholane-3α,7α,12α,24-tetrol (petromyzonol; PZ), PZS, 3kPZS, ACA and 3kACA were purchased from Toronto Research Chemicals (North York, ON, Canada) and dissolved at a concentration of 1 mg/mL in ethanol. Snail juice sulfatase, 3α-HSD, β-nicotinamide adenine dinucleotide (NAD), and 3-(Cyclohexylamino)-1-propanesulfonic acid (CAPS) were purchased from Sigma (St. Louis, USA). HPLC grade methanol, acetonitrile (ACN) and trifluoroacetic acid (TFA) were from Merck (Darmstadt, Germany). Deuterated dimethyl sulfoxide (DMSO) was obtained from Cambridge Isotope Laboratories (Andover, Mass.).

Animals

Adult sea lamprey were trapped or collected by hand from tributaries to lakes Huron and Michigan by the staff of the U.S. Fish and Wildlife Service, Marquette Biological Station (MBS), Marquette, Mich., USA. The animals were transported to the main laboratory at the U.S. Geological Survey, Lake Huron Biological Station, Millersburg, Mich. USA. These adults were held in flow-through tanks (1000 L) with Lake Huron water (7° C. to 20° C.).

Extraction of Pheromones from Water

A spermiating male lamprey was held for 4 h in a tank with 10 L lake water. The lamprey was then removed and the water passed through Whatman Grade 3 filter paper and then through Sep-Pak C18 cartridges (Waters, Milford, Mass., USA; 1 L of water per cartridge). After being washed with 5 mL deionized water, the cartridges were purged with 5 mL methanol. The methanol eluants were pooled and dried down using a rotary evaporator. 300 L of lamprey holding water from 30 sea lampreys was processed to obtain c. 2 mg of natural compound.

HPLC Fractionation and Analysis of Compounds

Extract equivalent to 20 L water was reconstituted in 720 μL of 0.01% TFA (v/v) and 280 μL of 70% ACN/0.01% TFA and loaded onto a reverse phase preparative HPLC column (Nova-Pak, 39×300 mm, Waters). The column was developed with: 20% ACN in 0.01% TFA for 10 minutes; a linear gradient from 20% to 70% ACN in 0.01% TFA for the next 50 min; and, 70% ACN in 0.01% TFA for the final 20 min. The flow rate was 4 mL/min and ultra-violet (U-V) absorption was monitored at 200 nm. Fractions were collected every 1 min. In experiments that were designed to compare the behavior of natural and synthetic compounds, an analytical reverse phase column (3.9×300 mm, Waters) was used at a flow rate of 0.5 mL/min.

TLC Analysis of Compounds

Thin layer chromatography (TLC) was performed on silica plates (LK6DF; Whatman). The solvent was a mixture of chloroform:ethanol:acetic acid (200:50:1 v/v/v). Samples and standards were run for 45 min. The plates were then dried, sprayed with 5% phosphomolybdic acid in ethanol (w/v) (Kritchevsky and Kirk, Arch. Biochem. Biophys. 35: 346–51 (1952)) and heated at 100° C. for c. 5 min.

Hydrolysis of the Sulfate Group of 3kPZS

Natural and synthetic 3kPZS (100 μg each) were dissolved in 500 μL 0.5 M sodium acetate buffer, pH 5.0, and incubated overnight at 37° C. with 1000 units of snail juice sulfatase (Dodgson and Powell, Biochem. J. 73: 666–71 (1959)). The reaction mixture was loaded onto a C18 Sep-Pak and eluted with 5 mL methanol. The methanol eluants were dried down and subjected to TLC and HPLC analyses.

Conversions with 3α-Hydroxysteroid Dehydrogenase

Enzymatic conversion of 3kPZS and ACA was performed by the method of Macdonald et al. (Anal. Biochem. 57: 127–36 (1974)) and Schwartz et al. (Chim. Acta. 50: 197–206 (1974)) with a slight modification. Natural 3kPZS, synthetic 3kPZS, and synthetic 3kPZ (100 μg each) were incubated with 1 unit of 3α-HSD and 2 mg NAD in 0.1 M Tris-HCl buffer, pH 7.2 for 2 hours. A control experiment was carried out by incubation of the compounds in 0.1 M Tris-HCl buffer, pH 7.2 without enzyme or NAD. The reactants were concentrated with a Sep-Pak cartridge, eluted with 5 mL methanol, and dried down. Enzymatic conversion of ACA to 3kACA was carried out by the method of Macdonald et al. (Macdonald et al., Anal. Biochem. 57: 127–36 (1974)). ACA (2 mg) was incubated for 2 h in 0.05 M CAPS buffer, pH 10.8 containing 20 mg NADH and 5 units 3α-HSD at 37° C. The reactants were concentrated with a Sep-Pak cartridge, eluted with 5 mL methanol, dried down, redissolved in 100 μL methanol, and subjected to TLC and HPLC.

Mass Spectrometry and Nuclear Magnetic Resonance

Mass spectra were obtained using a JEOL HX-110 double-focusing Fast Atom Bombardment (FAB) mass spectrometer (JEOL, Peabody, Mass., USA) which could be operated in either the positive or negative ion mode. Ions were produced by bombardment with a beam of Xe atoms (6 keV). The accelerating voltage was 10 kV and the resolution was set at 3000. Samples were prepared for mass spectrometry by drying down the HPLC fractions and re-dissolving them in methanol. High resolution mass spectrometry was performed by peak matching with a resolution of 10,000. FABMS was done at the NIH MS facility at MSU.

For Nuclear Magnetic Resonance (NMR) analysis, 3 mg each of ACA and 3kACA and ca. 2 mg of natural 3kACA were dissolved in 700 mL of deuterated DMSO. For assignment, 5 mg of synthetic 3kACA was dissolved in 700 mL of deuterated DMSO and performed series of NMR experiments that included dqf-COSY, HMQC, and HMBC. All spectra were run at 25° C. with a deuterium lock. The NMR analysis was done at the Max T. Rogers NMR Facility, Department of Chemistry, MSU using a VXR-S 500 MHz NMR Spectrometer (Varian Inc., Palo Alto, Calif.)

Results

HPLC Purification of Putative 3kACA

Figure 5:
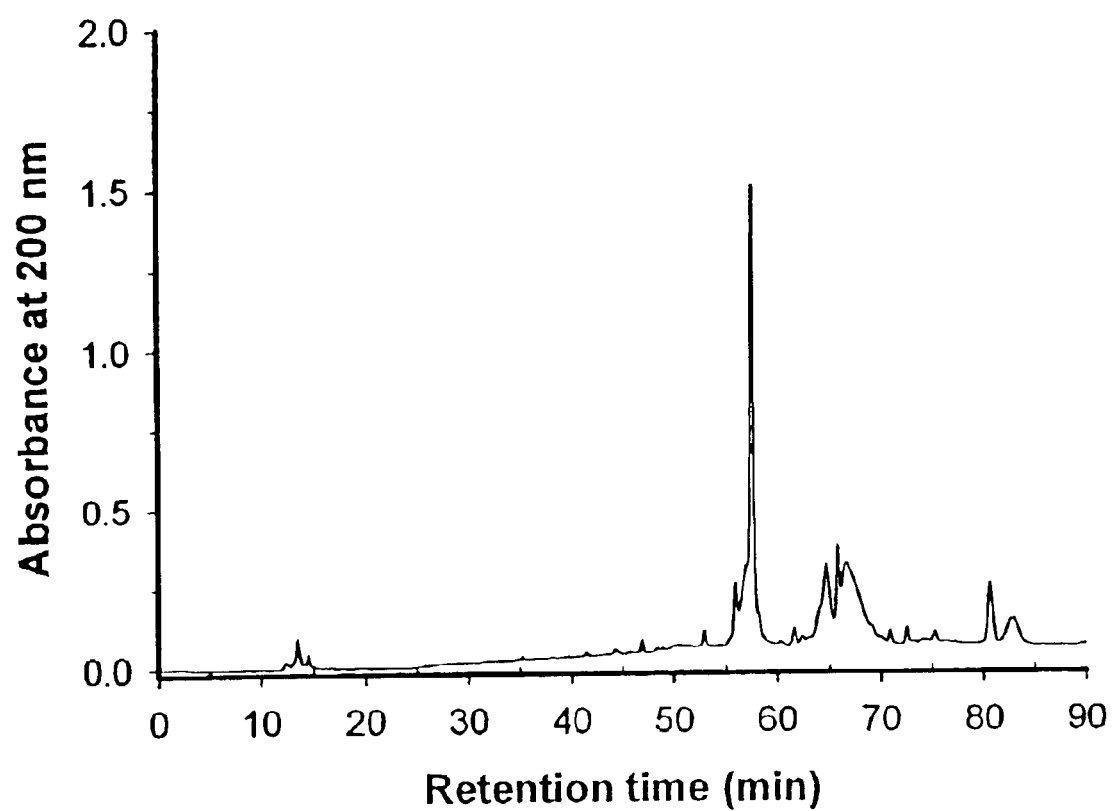
FIG. 5 shows the results of a re-purification of 3kACA on a preparative HPLC column.

Several batches of the second HPLC peak (shown as eluting at 58 min in Example 1) were pooled and rerun on the same preparative HPLC column (FIG. 5). Fractions eluting around 57 to 58 minutes, where there was a noticeable UV absorption peak at c. 200 nm, were dried down. The total amount of the compound that was obtained was c. 2 mg.

Mass Spectrometry of Natural and Synthetic 3kACA

Figure 6:
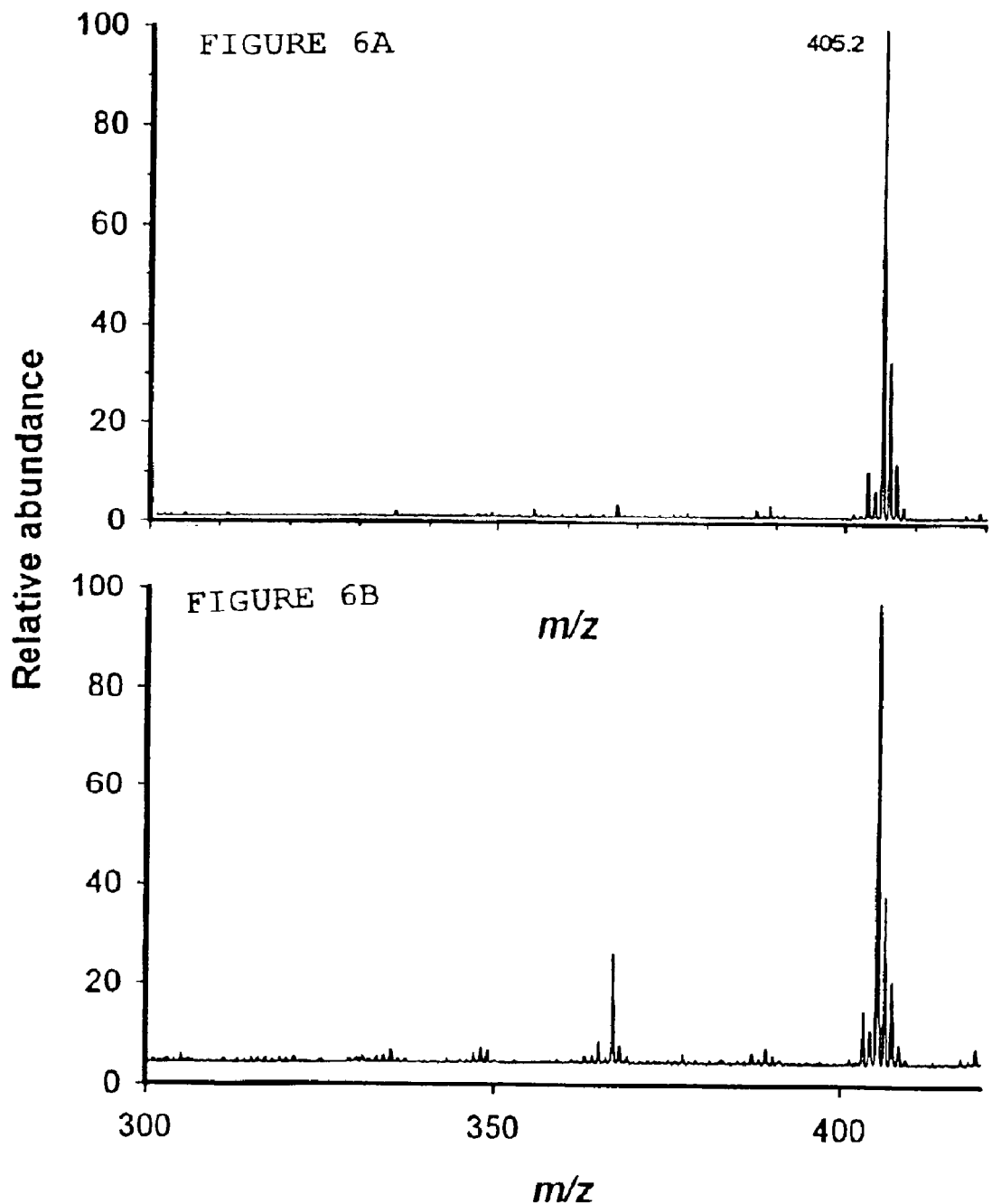
FIG. 6A shows a mass spectrometric analysis of fractions 58 from the HPLC shown in FIG. 1(A) subjected to FAB-MS analysis (negative mode) which indicated a mass of 406 Da.
FIG. 6B shows a mass spectrometric analysis of synthetic 3kACA subjected to FAB-MS analysis (negative mode) which indicated a mass of 406 Da.

Mass spectrometry showed that natural and synthetic 3kACA both had the same mass of 406 Dalton (FIGS. 6A and 6B). High resolution mass spectrometry analysis confirmed the molecular mass of the natural compound to the −2.5 ppm level (data not shown).

Chromatographic Behavior of Natural and Synthetic 3kACA

Figure 7:
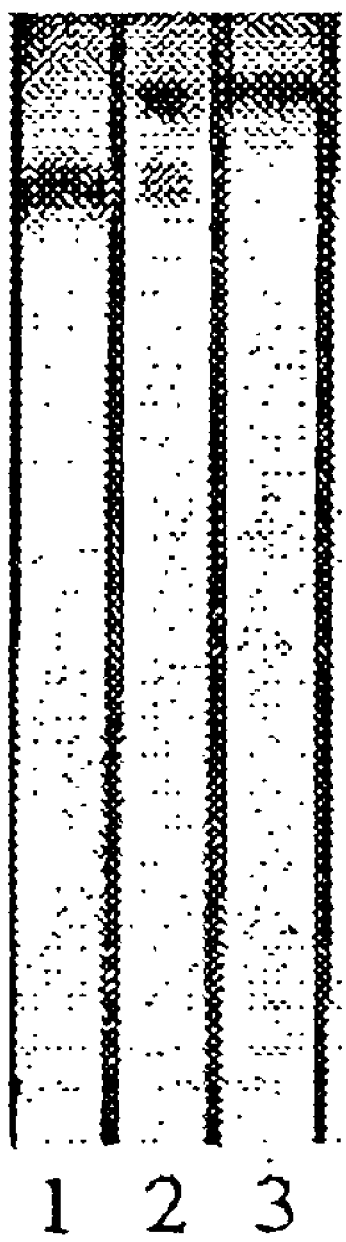
FIG. 7 shows a TLC separation of allocholic acid (lane 1), allocholic acid which had been treated with 3α-HSD and NAD (lane 2) and compound in fraction 58 of HPLC (lane 3).

ACA was treated with 3α-HSD and NAD. On TLC (FIG. 7), the main product was isopolar with natural 3kACA.

Some of the ACA was not converted. On HPLC (FIGS. 8A and 8B), the main peak of absorption of natural 3kACA ran in the same position as the main peak of absorption of synthetic 3kACA. The ability of 3kACA to adsorb UV at 200 nm is conferred by the double bond between the third carbon and the oxygen atom (i.e. the 3-keto group). Thus ACA, which has a 3α-hydroxyl group, does not show up on HPLC.

NMR Analysis of Synthetic and Natural 3kACA

Figure 9A:
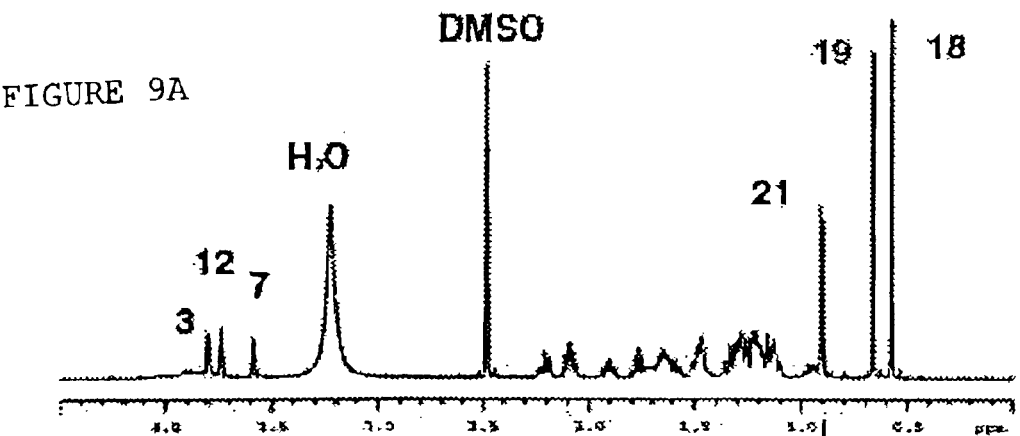
FIG. 9A shows a one-dimensional $^{1}$H-NMR analysis of synthetic allocholic acid. The numbers refer to the peaks representing the C-18, C-19 and C-21 methyl groups which are found in all 3α-hydroxylated bile acids. In the case of there being a 3-keto group, the C-19 peak shifts to overlie the C-21 peak. This can be seen in 9B and 9C.
Figure 9B:
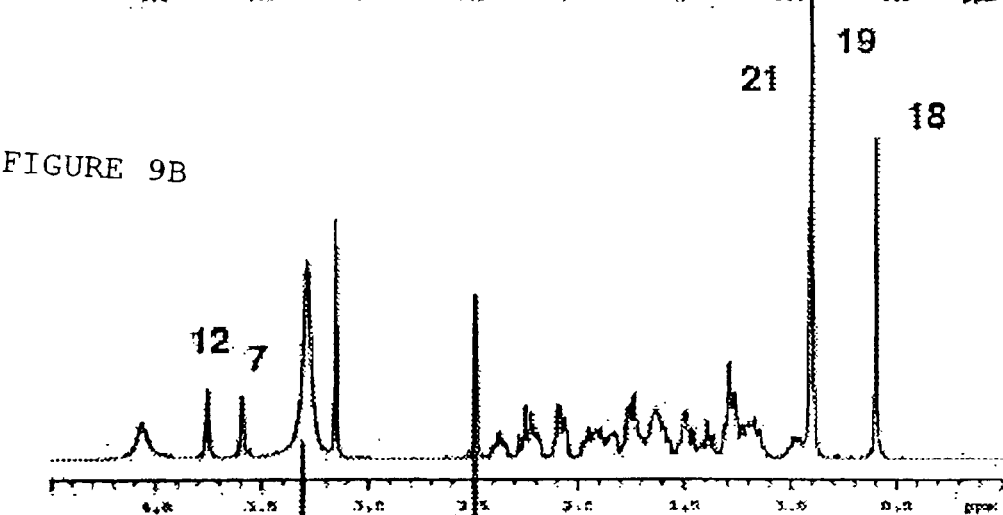
FIG. 9B shows a one-dimensional $^{1}$H-NMR analysis of synthetic 3-keto allocholic acid. The peak ascribable to the 3α-hydroxyl group is missing. The positions of all but a few trace peaks in 9B and 9C are identical between 0.5 ppm to 4.5 ppm. The positions of all but a few trace peaks in 9B and 9C are identical between 0.5 ppm to 4.5 ppm.
Figure 9C:
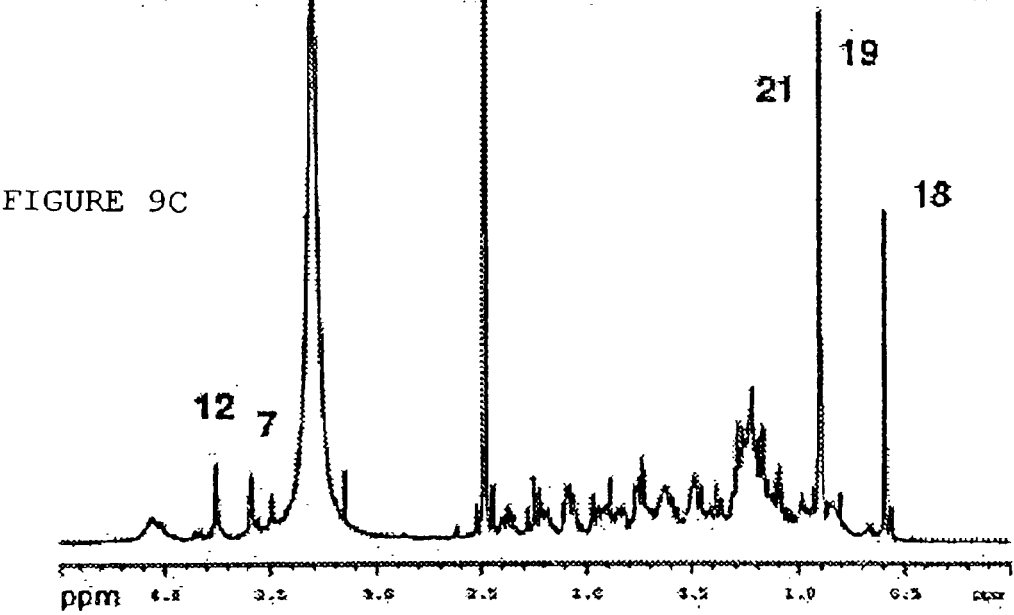
FIG. 9C shows a one-dimensional $^{1}$H-NMR analysis of HPLC fraction 58. The positions of all but a few trace peaks in 9B and 9C are identical between 0.5 ppm to 4.5 ppm.

One- and two-dimensional $^1$H-NMR analysis of natural and synthetic 3kACA further confirmed the chemical identity of the natural compound. The chemical shifts which are characteristic of other bile acids (Waterhous et al., J. Lipid Res. 26: 1068–78 (1985); Ishikawa et al., J. Lipid Res. 40: 1920–4 (1999)) were clearly visible in the one-dimensional $^1$H-NMR spectra of natural 3kACA, synthetic 3kACA, and synthetic ACA (FIGS. 9A, 9B, and 9C). These included: the C-18 (0.592 ppm), C-19 (0.904 ppm), and C-21 (0.894 ppm) methyl groups; the 7α-hydroxyl (3.59 ppm) and 12α-hydroxyl (3.76 ppm) groups in 3kACA, and the extra 3α-hydroxyl (3.82 ppm) group in ACA. The C-19 methyl proton peak of ACA at 0.68 ppm had shifted to overlap with the C-21 methyl group at 0.90 ppm in 3kACA. This was demonstrated by peak integration, which revealed double the number of protons (6) in the peak at 0.90 ppm in comparison to those (3) in the peak at 0.59 ppm in both natural and synthetic 3kACA. The "hidden" C-19 methyl group in one-dimensional $^1$H-NMR was clearly visible in the 2D HMQC NMR spectrum (data not shown). In addition, 2D-HMQC analyses confirmed that both natural and synthetic 3kACA displayed exactly the same chemical shift for major functional groups (data not shown). Combined application of several NMR techniques were made to assign all the carbon and proton shifts for synthetic 3kACA (Table 3). The majority of carbon resonances were between 10 to 80 ppm except for C-24 (carboxyl) and C-3 (carbonyl), which had shifts of 174 ppm and 210 ppm, respectively.

TABLE 3

$^{13}$C and $^1$H resonance assignments for 3-keto allocholic acid.

| Number | Type | Carbon | Proton |
|---|---|---|---|
| 1 | CH2 | 22.67 | 1.64, 1.67 |
| 2 | CH2 | 43.96 | 1.75, 2.25 |
| 3 | C | 210.62 | — |
| 4 | CH2 | 28.83 | 1.50, 1.50 |
| 5 | CH | 41.35 | 1.88 |
| 6 | CH2 | 36.81 | 1.27, 1.41 |
| 7 | CH | 65.39 | 3.59 |
| 8 | CH | 46.04 | 1.75 |
| 9 | CH | 38.85 | 1.92 |
| 10 | C | 34.90 | — |
| 11 | CH2 | 27.09 | 1.16, 1.75 |
| 12 | CH | 70.82 | 3.76 |
| 13 | C | 45.76 | — |
| 14 | CH | 38.16 | 1.60 |
| 15 | CH2 | 30.78 | 2.07, 2.25 |
| 16 | CH2 | 30.71 | 1.22, 1.64 |
| 17 | CH | 39.49 | 1.29 |
| 18 | CH3 | 9.96 | 0.89 |
| 19 | CH3 | 12.28 | 0.60 |
| 20 | CH | 34.95 | 1.28 |
| 21 | CH3 | 16.85 | 0.88 |
| 22 | CH2 | 37.86 | 1.82, 1.87 |
| 23 | CH2 | 37.67 | 2.08, 2.37 |
| 24 | C | 174.83 | — |

Elution Position of Natural and Synthetic 3kPZS on HPLC

Both natural and synthetic 3kPZS (100 µg each) were run separately or combined (50 µg of each) on the analytical HPLC column. In all cases, the main peak of U-V adsorption (200 nm) appeared in the same fractions (FIGS. 10A, 10B, and 10C). Both compounds were also isopolar on TLC (data not shown).

Hydrolysis of the Sulfate Group of 3kPZS

Figure 11:
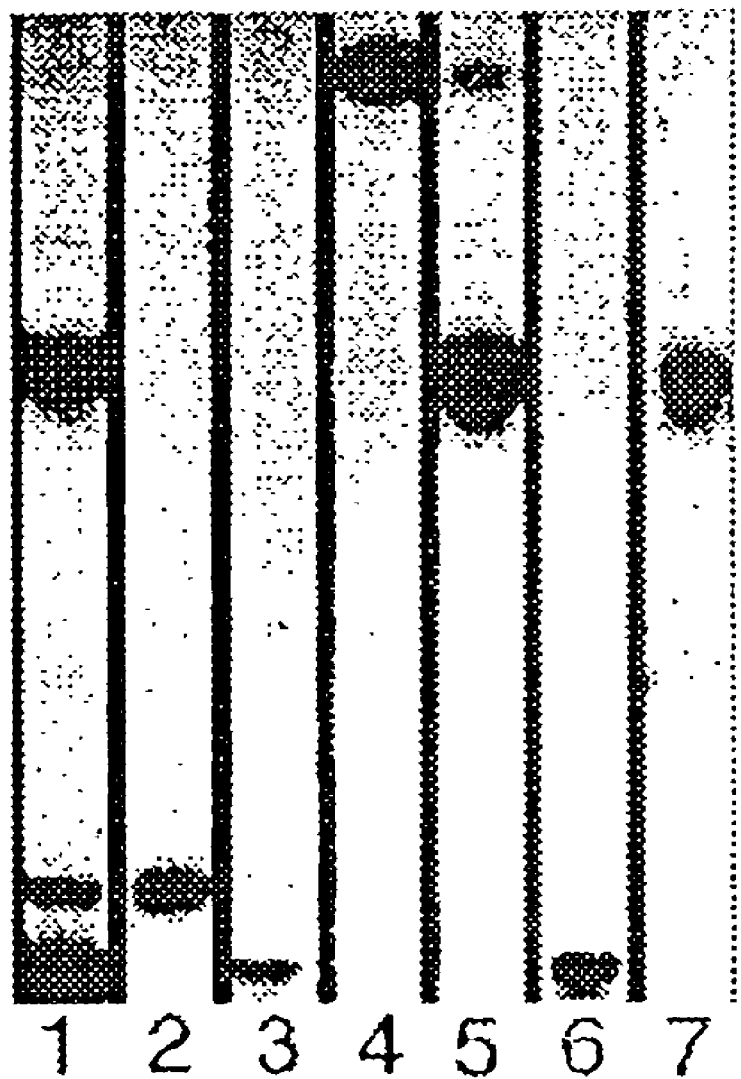
FIG. 11 shows a TLC separation, after treatment with 3α-HSD and NADH, of natural 3kPZS (lane 1), synthetic 3kPZS (lane 3), 3kPZS (Lane 5), PZS (Lane 6) and PZ (Lane 7). Untreated 3kPZS and 3-keto petromyzonol (3kPZ) were run in lanes 2 and 4, respectively. Note that PZS and petromyzonol (PZ) were unaffected by the enzyme treatment as C-3 already possesses a hydroxyl group.

Sulfatase treatment of natural and synthetic 3kPZS (either separately or as a mixture) resulted in the appearance of a new U-V-absorbing peak which had the same elution position as 3kPZ (FIG. 11). In all cases, hydrolysis was incomplete as there was a peak which remained in the position of the standard.

3α-HSD Conversion of 3kPZS to PZS

Figure 12:
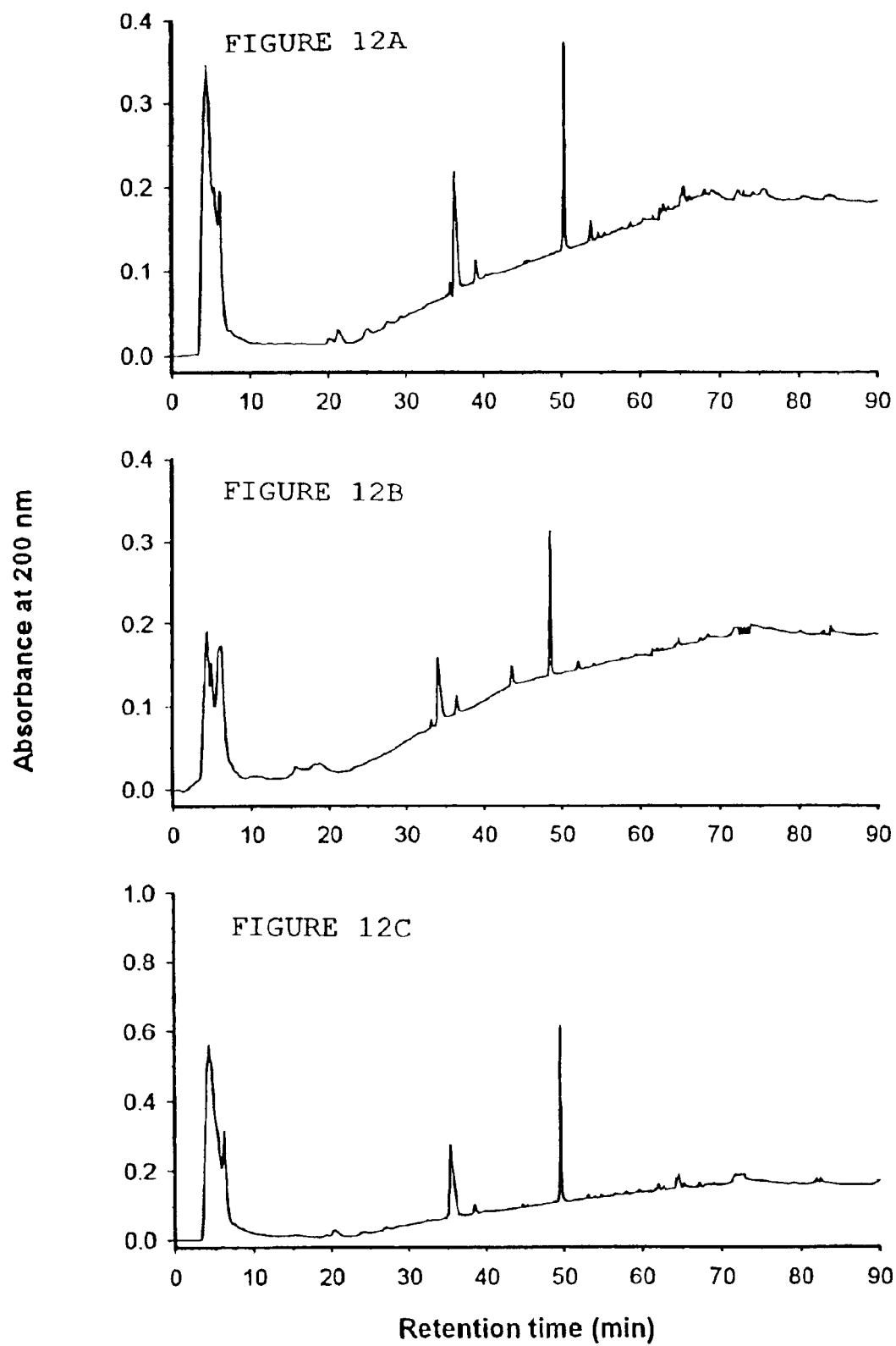
FIG. 12A shows an HPLC separation, after treatment with snail juice sulfatase of synthetic 3kPZS. Hydrolysis was incomplete and the peak at 34/35 min represents undigested 3kPZS and that at 49/50 min 3kPZ.
FIG. 12B shows an HPLC separation, after treatment with snail juice sulfatase of natural 3kPZS. Hydrolysis was incomplete and the peak at 34/35 min represents undigested 3kPZS and that at 49/50 min 3kPZ.
FIG. 12C shows an HPLC separation, after treatment with snail juice sulfatase of a mixture of synthetic and natural 3kPZS. Note that both compounds behave identically.

Treatment of synthetic and natural 3kPZS with 3α-HSD and NAD at pH 7.2 converted all of the synthetic compound and most (phosphomolybdic acid-stained spots on TLC are not quantifiable) of the natural compound into compounds which had the same polarity as PZS (FIGS. 12A, 12B, and 12C). Unexpectedly, some hydrolysis of the sulfate group appeared to have occurred in the natural compound as there was also a faint spot in the elution position of 3kPZ and a prominent spot in the elution position of PZ. Synthetic PZ and PZS were unaffected by treatment with 3α-HSD under the same conditions, while synthetic 3kPZ was mostly converted to a compound with the same polarity as PZ.

Discussion

Identification of 3kACA

The study in Example 1 wherein 3kPZS was identified as the major pheromone of spermiating male lampreys showed that at least two other compounds were released concurrently into the water and that one of them appeared to have electro-olfactographic (EOG) activity. Following the development of an ELISA for 3kPZS, this particular compound was found to cross-react in the assay and also to elute in the same position as synthetic 3kACA on HPLC. The present study, through the use of mass spectrometry, NMR, HPLC, TLC and enzymatic modification, confirms this identification. The amount of compound which was used in this study was only about 2 mg and this was extracted from c. 300 L of water. The amount of 3kPZS which could be extracted from the same volume of water was in excess of 50 mg. This is in agreement with the ELISA results—which indicated that the ratio of 3kPZS to 3kACA was c. 20:1.

The strongest evidence for the identify of 3kACA was provided by NMR analysis which indicated the presence of all the major functional groups which have been found in previous NMR studies on bile acids and steroids (Example 1; Barnes and Geckle, J. Lipid Res. 23: 161–70 (1982); Waterhous et al., J. Lipid Res. 26: 1068–78 (1985); Ishikawa et al., J. Lipid Res. 40: 1920–4 (1999)). The resonance of one carbon was found to be 210 ppm, suggesting the existence of a keto group. The chemical shift of the C-19 methyl group of 3kACA (by +0.23) compared to that of ACA, indicating the keto group is formed at C-3 (that has previously been shown to cause a chemical shift of the C-19 methyl group by +0.242 ppm; (Bhacca and Williams, In: Applications of NMR spectroscopy in organic chemistry: illustrations from the steroid field. San Francisco, Holden-Day, Inc., pp. 13–41 (1964)). In addition, 7α and 12α OH groups were also identified from NMR spectra in both natural and synthetic 3kACA.

The concurrence of 3kACA and 3kPZS in water extracts from spermiating males has a strong parallelism with the concurrence of ACA and PZS in water extracts from larval lampreys (Polkinghorne et al., Fish Physiol. Biochem. 24: 15–30 (2001)) although the ratio of PZS to ACA (3:1) in larvae was lower than that of 3kPZS to 3kACA in spermiating males. In larvae, there is strong evidence that a mixture of PZS and ACA has a much stronger pheromonal effect than either compound alone (Bjerselius et al., Can. J. Fish Aquat. Sci. 57:557–69 (2000)). Whether this is the case for a mixture of 3kACA and 3kPZS in spermiating males remains to be established. However, it does seem likely. In insects, it is well known that pheromonal signals most often consist of multicomponent mixtures and that at least two principal pheromone components seem to be necessary for eliciting attraction responses (Mustaparta, In: Carde RT, Minks AK, editors. Insect pheromone research: new directions. New York: Chapman & Hall, pp. 144–63 (1997)). For example, *Heliothis virescens* produce (Z)-11-hexadecennal and (Z)-9-tetradecenal in the ratio of 16:1 and species *Helicoverpa zea* produce the same compounds in the ratio of 16:0.1 (Pope et al., J. Insect Physiol. 30: 943–45 (1984); Teal et al., J. Chem. Ecol. 12: 107–25 (1986)). However, in some species, ratios from between about 10:1 to 100:1 have been found to elicit responses (Kehat and Dunkelblum, J. Insect Behavior 3: 75–83 (1990)).

Further Identification Studies on 3kPZS

In Example 1, only a small supply of synthetic 3kPZS had been produced by enzymatic oxidation of the 3α-hydroxyl group of PZS. This restricted the number of comparisons that could be made between the natural and synthetic 3kPZS. This example completes these studies. This example confirms that both synthetic and natural 3kPZS have the same chromatographic properties and behave in the same way when treated with 3α-HSD and sulfatase. The only difference noted was that a proportion of the natural compound appeared to have broken down to 3kPZ (which was then converted to PZ by the 3α-HSD). The reason for this has not been fully established. However, the natural compound that was used in this example had been stored at 1 mg/mL in ethanol at −20° C. for over one year, whereas the synthetic compound had been made up freshly. The possibility is that the sulfate group is unstable in long-term storage.

4.3 Relationship Between Adult and Larval Bile Acids and Alcohols

It seems likely that the pathway of biosynthesis that is responsible for producing PZS and ACA in the larvae is the same as that responsible for producing 3kPZS and 3kACA in spermiating males. As mentioned previously, there is only one difference between the two sets of compounds; and this difference only needs the intervention of one enzyme: 3α-HSD. This is a widespread enzyme in steroid-producing tissues (Talalay, Meth. Enzymol. 5:512–26 (1962)). Because bile acids and alcohols are derived from cholesterol and cholesterol already has a 3α-hydroxyl group, it is more likely that PZS and ACA are precursors of 3kPZS and 3kACA than vice versa. Although the oxidation of 3α-hydroxyl bile acids to 3-keto bile acids does not appear to be common in vertebrates, a low rate of production of 3-keto bile acids has been demonstrated in the liver of the guinea pig and hamster (Hofmann, In: Arias, Boyer, Fausto, Jakoby, Schachter, Shafritz, Eds. The Liver: Biology and Pathobiology, Third Edition. New York: Raven Press Ltd, pp. 677–718 (1994)).

Because adult lampreys often enter streams with abundant larvae to reproduce, larval and spermiating male bile acids and alcohols will both be present in stream water during the spawning season. In order to recognize and distinguish between the two sets of compounds, ovulated female lampreys must have evolved at least two sets of olfactory receptors. The characteristics of these receptors are currently under investigation. However, Li and Sorenson (J. Comp. Physiol. A. 180: 429–38 (1997)) have already shown that the olfactory epithelia of sea lamprey have separate and independent olfactory receptors for different types of bile acids. Thus, it would not be unexpected that they can readily distinguish between PZS and 3kPZS (and between ACA and 3kACA) despite the small difference between the compounds.

In summary, a new bile acid, 3kACA, has been definitively identified in water washings of spermiating male lamprey. Since the HPLC fractions in which this compound elutes also have EOG activity, it is possible that it enhances or in some other way modifies the pheromonal activity of 3kPZS. Also presented in this example is some previously unpublished evidence that the 3-keto group of both natural and synthetic 3kPZS can be converted to a 3α-hydroxyl group by 3α-HSD; and that the sulfate group can be removed by enzymatic hydrolysis.

EXAMPLE 3

An enzyme-linked immunosorbent assay (ELISA) has been developed for a conjugated bile acid, 7α,12α,24-trihydroxy-5α-cholan-3-one-24-sulfate (3-keto petromyzonol sulfate (3kPZS)). A polyclonal antiserum against the pheromone was raised by injecting 3-keto-petromyzonol-24-hemisuccinate (3kPZ-HS) conjugated to bovine serum albumin into rabbits. The enzyme label was prepared by conjugating 3kPZ-HS to acetylcholinesterase. The standard curve had a working range of 20 pg to 10 ng per well. Intra- and inter-assay variations were less than 5% and 12%, respectively. The antiserum had 100% cross-reaction with 3-keto petromyzonol and 3-keto allocholic acid but less than 0.2% cross-reaction with petromyzonol, allocholic acid, cholic acid, and taurolithocholic acid sulfate. A 1.6% cross-reaction was found with petromyzonol sulfate (which was, however, found to be contaminated with 3kPZS). The assay was applied to water which had been conditioned for 4 h by either larvae, parasitic juveniles, ovulating females, pre-spermiating males or spermiating males. Immunoactive material (average 200 ng/mL, which is equivalent to 500 μg animal/h) was only found in water from the spermiating males. It diluted parallel with the standard curve. On High Performance Liquid Chromatography, the immunoactive material separated into two peaks, the larger (>95%) of which corresponded to the elution position of 3kPZS and the smaller to the elution position of 3-keto allocholic acid. The latter could be extracted from the water, at pH 4, with diethyl ether. Assay of water samples collected from "bisected" male lampreys also established that 99.6% of the immunoactive material emanated from the front end of the fish. This assay has applications in both physiological and ecological aspects of sea lamprey reproduction.

Materials and Methods
Chemicals and Equipment

3kPZS, 3kPZ, petromyzonol (PZ), PZS, ACA, and 3-keto allocholic acid (3kACA) were purchased from Toronto Research Chemicals Inc. (2, Brisbane Road, North York, Ontario, Canada M31 218). AChE, acetylthiocholine, cholic acid (CA), 5,5'-dithio-bis-2-nitrobenzoic acid (DTNB), dimethylformamide (DMF), taurolithocholic acid sulfate, trypsin, and bovine serum albumin (BSA) were obtained from Sigma (St Louis, Mo.). Freund's complete and incomplete adjuvants for immunization were also obtained from Sigma. The assay was performed in 96-well polystyrene high-binding microtiter plates (Costar, product code 3590) from Corning (Acton, Massachusetts). The plates were read with a Bio-Rad Benchmark plate reader (Hercules, Calif.) at 405 nm. Sep-Paks were purchased from Waters (Milford, Mass.) and PD-10 desalting columns from Pharmacia (Piscataway, N.J.). HPLC was carried out on a Nova-Pak HR C18 column (Waters, 19×300 mm) using a Waters pump system. The fractionation was monitored using a Photodiode Array detector (Waters) at 200 nm.

Preparation of Antibody

For the preparation of antigen, 3-keto petromyzonol-hemisuccinate (3kPZ-HS) was custom synthesized by Toronto Research Chemicals. To conjugate it to BSA, 21 mg of 3kPZ-HS was dissolved in 1.5 mL of dimethylformamide (DMF) in a 20 mL glass beaker. The beaker was placed in crushed ice within a polystyrene container that was placed on top of a magnetic stirrer. A small magnetic flea was added to the beaker. The ice was prevented from thawing by the occasional addition of small amounts of liquid nitrogen to the container. With constant stirring, 12 $\mu$L tri-butylamine and 10 $\mu$L isochloroformate were added to the beaker and the reaction allowed to proceed for 40 min. In the meantime, 80 mg BSA was dissolved in 3 mL distilled water, diluted with 3 mL DMF plus 1 drop of 2N sodium hydroxide and chilled on ice.

This mixture was added to the beaker and left to stir for a further 3 h. After this time, the mixture, which was slightly opaque, was centrifuged for 10 min at 1000×g. The clear supernatant was divided into 2.5 mL aliquots for desalting on PD-10 columns (Nash et al., Fish Physiol. Biochem. 22: 355–363 (2000)) using distilled water to elute the protein fraction. The eluants were combined, frozen and freeze-dried.

To produce antisera, 6 mg of the powdered conjugate was dissolved in 1 mL 0.9% saline and mixed with 1 mL Freund's complete adjuvant. One mL antigen-adjuvant mixture was injected into four rabbits. The rabbits were boosted with the conjugate in Freund's incomplete adjuvant two weeks after the first injection. They were bled for the first time at four weeks after the first injection. The serum was collected by centrifugation of the blood at 2700 rpm for 15 mm. The supernatant was removed, aliquoted, and stored at −80° C.

Preparation of Enzyme Label

The preparation of the enzyme label was based on the procedure described by Nash et al. (2000) with slight modifications. Briefly. G4-acetylcholinesterase was generated by treating AChE (1 mg) in 500 $\mu$L 0.1 M sodium phosphate buffer, pH 7.0 with 25 $\mu$L trypsin solution at 25 $\mu$g/mL in the same buffer for 24 h at room temperature. This reaction mixture was loaded on to a PD-10 column and eluted with 3.5 mL of 0.1 M borate buffer, pH 8.5. Next, 3kPZ-HS was activated by dissolving 200 $\mu$g in 38 $\mu$L of N-hydroxysuccinimide solution (1 mg/mL in DMF) and then adding 32 $\mu$L of N,N'-dicyclohexylcarbodiimide solution (2 mg/mL in DMF) and leaving it overnight in the dark. Thirty microliters of this reaction mixture was reacted with 400 $\mu$L G4-AChE stock for 2 h in the dark. This was purified on a PD-10 column by eluting with 3.5 mL of 0.01 M Tris buffer, pH 7.4 containing 0.01 MgCl$_2$, 1M NaCl, and 0.15 mM NaN$_3$. The eluant was stored at −20° in 20 $\mu$L aliquots.

Titration of Antibody and Enzyme Label

The optimum dilutions of AChE label and antibody were determined by checkerboard titration (Diamanis and Christopoulos, In Immunoassay, Academic Press, San Diego. (1996)). The starting dilutions for the titration of the AChE label and the antiserum were 1:40 and 1:1000, respectively.

Assay Procedure

Plates were coated with polyclonal goat anti-rabbit IgG (Sigma; product code R2004) by adding 120 $\mu$L of antibody diluted in 0.05 M potassium phosphate buffer, pH 7.4 to each well and incubating overnight at 4° C. The plates were blocked by addition of 100 $\mu$L of 3% BSA in 0.1 M potassium phosphate buffered saline and storage at 4° C. for at least 12 h.

After washing the plates three times with wash buffer (0.05 M potassium phosphate buffered saline, pH 7.4, 0.05% Tween 20), 100 $\mu$L of assay buffer (0.1 M potassium phosphate buffered saline, pH 7.4, 0.1% BSA, 1 mM EDTA, 0.15% sodium azide) was added to each well and serial dilutions of 3kPZS were made in a range of 20 $\mu$g to 10 ng/well. Non-specific binding (NSB) and maximum binding (B$_0$) were measured in separate wells. Water washings, extracts, or HPLC fractions were diluted 20 times in assay buffer and 100 $\mu$L added to wells in duplicate; 50 $\mu$L of the diluted enzyme label (1:2000) was added to all wells and 50 $\mu$L of primary antibody (1:500,000) was added to all but NSB wells. Plates were incubated for 2 h at room temperature in a humid chamber. Then, after rinsing three times with wash buffer, 200 $\mu$L Ellmans reagent (4.3 mg DTNB, and 4 mg acetyl thiocholine in 20 mL 0.02 M potassium phosphate buffer) was added to each well. The plates were sealed and incubated overnight at room temperature in a humid chamber. Color development was measured at 405 nm.

Assay Validation

To test the cross-reactivity of the antibody to structurally related compounds, serial dilutions of ACA, PZ, PZS, CA, 3kACA, and 3kPZ were assayed alongside the 3kPZS standard.

Intra-assay variation was determined by assaying eight replicates of 3kPZS standard in the same plate. Inter-assay variation was determined by assaying a sample six times in different plates. In addition, parallelism was determined by diluting water washing samples alongside 3kPZS.

HPLC Fractionation of Extracts

Up to 12 L of water which had been conditioned with spermiating male lampreys was pumped through twelve Sep-Paks (1 L each), which were then washed with distilled water and eluted with 5 mL methanol. The methanol was dried down in a rotary evaporator and the residue redissolved in 280 $\mu$L solvent B (70% acetonitrile and 0.01% TFA in deionized water) and 720 $\mu$L solvent A (0.01% TFA $\mu$L distilled water) and loaded on to the HPLC column. The column was developed with a gradient of solvent B from 28% to 100% over 50 minutes, at a flow rate of 4 mL/min. One min fractions were collected and diluted in assay buffer.

Separation of 3kPZS and 3kACA

A trial was carried out in which a mixture of synthetic 3kPZS and 3kACA was dissolved in buffers of different pH and then extracted with diethyl ether. This established that synthetic 3kACA, but not 3kPZS, could be extracted into the diethyl ether phase at pH 4. Based on this observation, an extract from 1 L of water that had been conditioned by a spermiating male was redissolved in 100 μL methanol and 900 μL of 0.05 M sodium acetate buffer, pH 4.0. This was extracted four times with 3 mL diethyl ether. The residue was then separated by HPLC as described above and the fractions assayed with the ELISA. Some of the extract which had not been treated with diethyl ether was treated in the same way. After these separations had been performed, standard synthetic 3kACA, 3kPZS and 3kPZ (200 μg each) were run on the column under identical conditions.

To measure the actual amounts of 3kPZS in the water samples which had been collected from spermiating males, 100 μL of water was mixed with 100 μL of 0.05 M sodium acetate buffer, pH 4.0, and the mixture was extracted 3 times with 700 μL of diethyl ether. 50 μL of the mixture after ether extraction was assayed. The ether extract was dried down, reconstituted in buffer and assayed to establish the amounts of 3kACA-like material present in the water.

Comparison of Different Life History Stages

Ten spermiating males, six pre-spermiating males, six parasitic stage adults and six ovulated females were kept separately in 10 L container filled with lake water. Six larval lampreys were kept separately in 250 mL. After 4 h, 20 mL samples of water were taken and frozen for subsequent direct assay.

Confirming the Route of Release of the Pheromone

Water was collected separately from the head and tail regions of spermiating male sea lampreys. To achieve this, an acrylic plate, with a hole that was slightly larger than the girth of an adult lamprey, was glued into the middle of an acrylic aquarium (thus creating two chambers). The hole was lined with a latex robber gasket, so that when a lamprey was pushed gently through the hole (to a position just behind the gills), water could not flow from one chamber into the other. A perforated acrylic tube was mounted on one side of the plate to immobilize the head of the animal. A flexible plastic mesh tube, with an adjustable width, was mounted on the other side. Once the lamprey had been secured, the head chamber was filled with 10 L of water. The tail chamber was inspected for leaks from the head end then also filled with 10 L of water. Air-stones were placed in both chambers and the male was held this way for 1 h. The water was collected at the end of this time and stored at −800 until analyzed. This procedure was carried out five times on separate fish.

Results

Enzyme Label and Antibody Production

All bleeds from all four rabbits were found to bind the enzyme label. The one with the highest titer (L286) was chosen for further development. Checkerboard titration of the antiserum and enzyme label determined that the optimal combination of dilutions was 1:500,000 for the antiserum and 1:2000 for AChE tracer, respectively.

Standard Curve and Assay Validation

Figure 13:
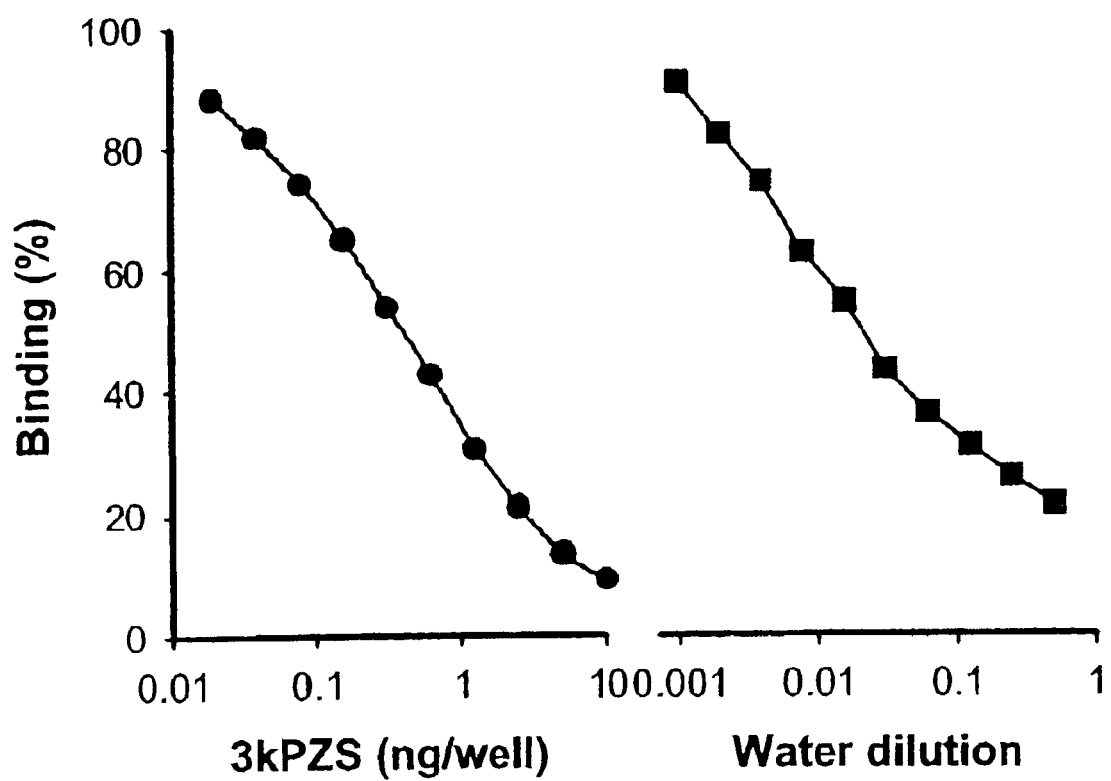
FIG. 13 shows dilution curves for synthetic 3kPZS and for water which had been conditioned by a spermiating male.

A standard curve was established in a working range of 20 pg/well to 10 ng/well. Close parallelism was observed between dilutions of water conditioned by a spermiating male and synthetic standard (FIG. 13). The intra-assay coefficient of variance was 5% and that for inter-assay 12% (for a sample in the middle of the standard curve).

Cross-Reaction of Other Compounds

Figure 14:
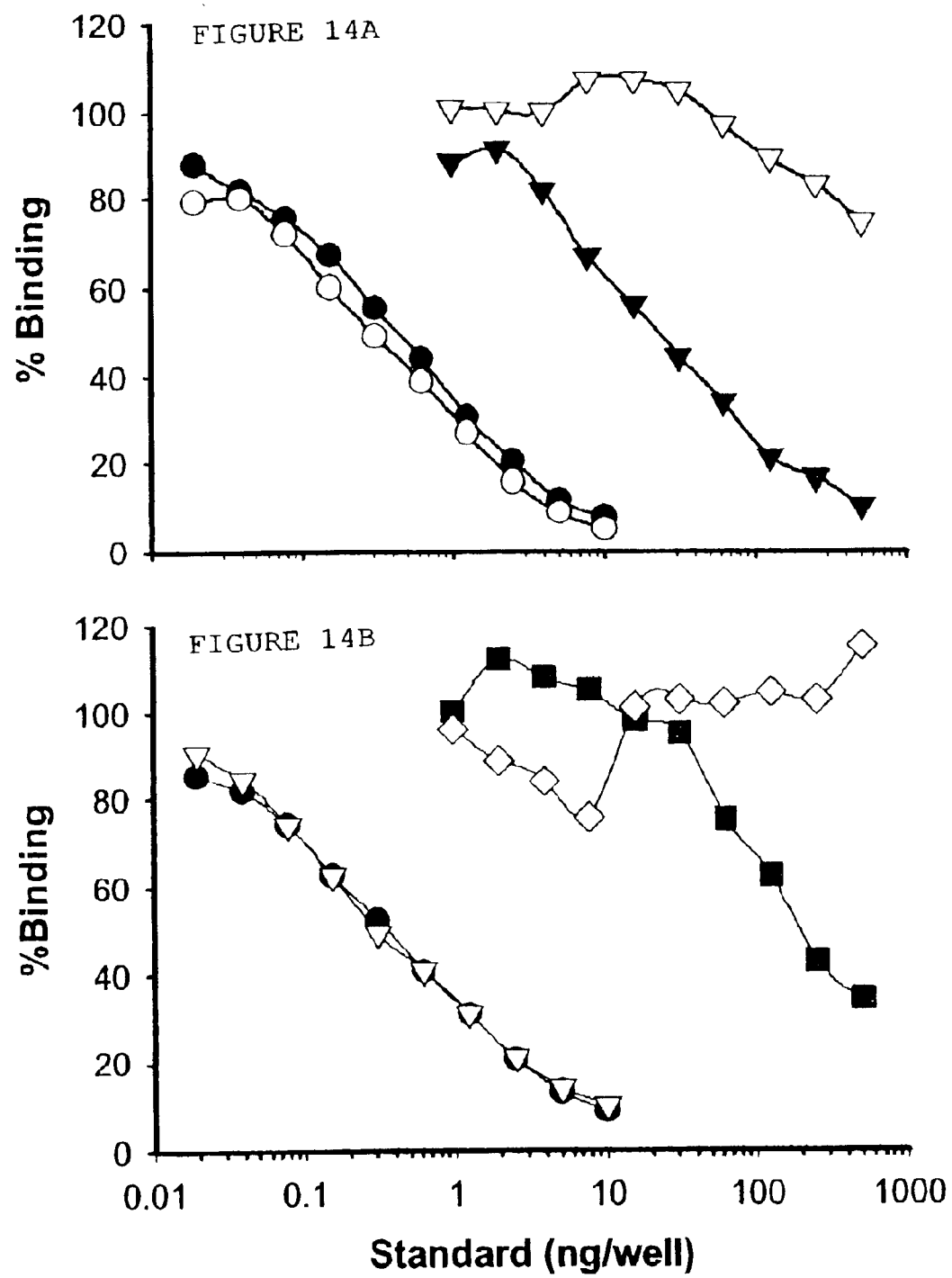
FIG. 14A shows the cross-reaction of the antiserum with 3kPZS (●), 3kPZ (○), PZS (▼), and PZ (▽).
FIG. 14B shows the cross-reaction of the antiserum with 3kPZS (●), 3kACA (▽), ACA (■), and CA (◇).

On a weight for weight basis, the antiserum cross-reacted equally well with 3kPZS, 3kPZ, and 3kACA (FIGS. 14A and 14B). The fact that 3kPZ and 3kACA are smaller molecules, however, implies that they do in fact cross-react slightly more strongly than 3kPZS. Cross-reaction with all the other compounds, except PZS (1.6%), was negligible. However, when the PZS was run on HPLC, the cross-reacting material was found in the elution position of 3kPZS (39 to 41 min) and none in the elution position of PZS (43 to 44 min).

Assay of HPLC Fractions

Figure 15:
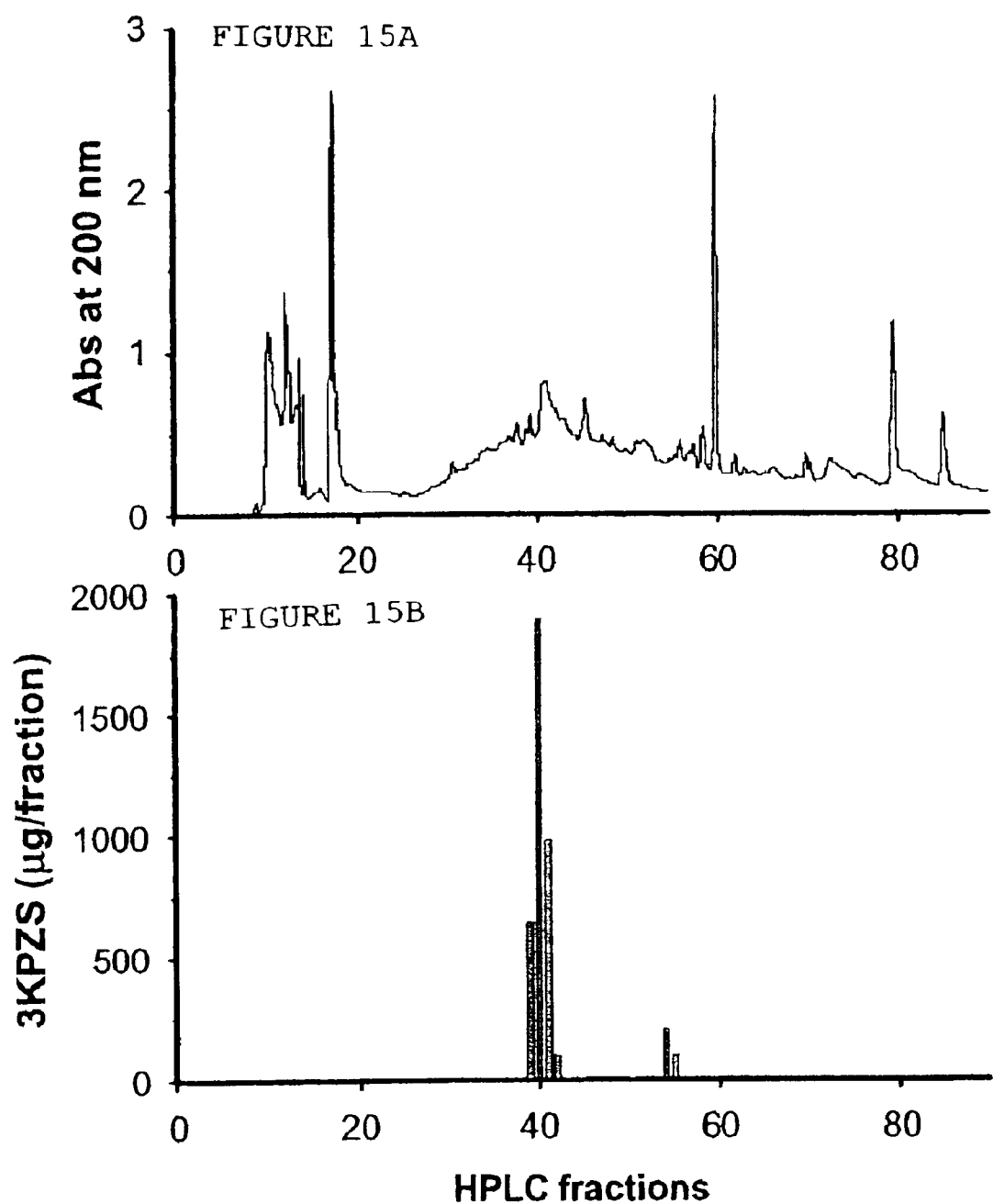
FIG. 15A shows a UW at 200 nm profile of the HPLC fractionation of an extract of water which had been conditioned by spermiating male lampreys.
FIG. 15B shows an immunoactivity profile of the same fraction of 15A after diethyl ether extraction at pH 4.0.

When assays were carried out on HPLC fractions of a water extract, the bulk of immunoactivity was found in fractions 39 to 41 (FIGS. 15A and 15B). The total amount of activity in all three fractions was 3.6 mg (which from 20 L water equates to an original concentration of c. 300 ng/mL in the water). Another small peak of immunoactivity was found in fractions 54 to 55.

HPLC Analysis of Synthetic Compounds

Figure 16:
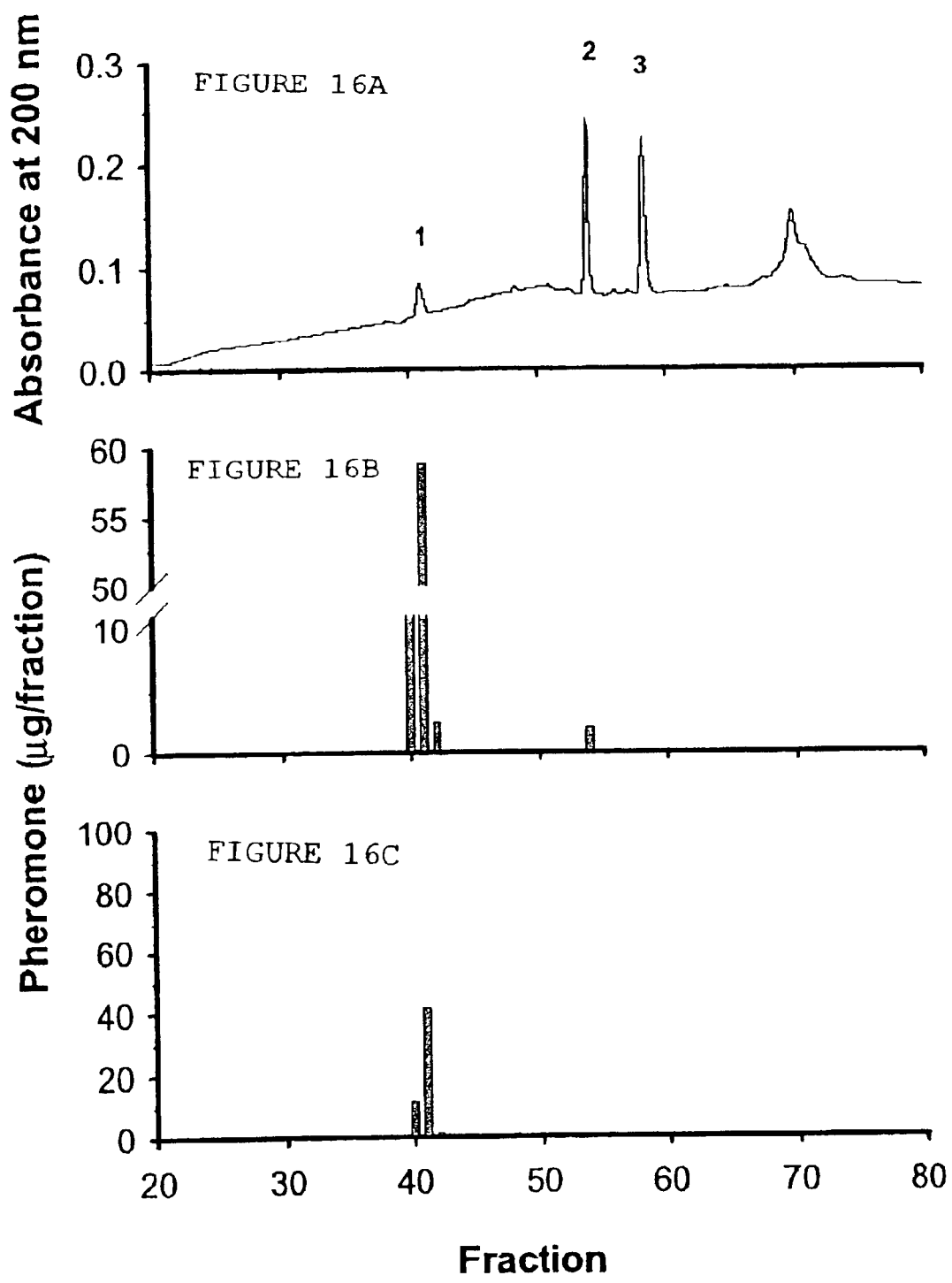
FIG. 16A shows a UV adsorption profiles of an HPLC fractionation of synthetic 3kPZS (peak 1), 3kACA (peak 2), and 3kPZ (peak 3).
FIG. 16B shows an immunoactivity profile of an HPLC fractionation of an extract of water from a spermiating male.
FIG. 16C shows an immunoactivity profile in the extract of 16B after diethyl ether extraction at pH 4.0.

The three synthetic compounds which cross-reacted with the antiserum were run on HPLC (FIG. 16A). Their elution positions were confirmed by UV absorption as: 3kPZS, 40 to 41 min; 3kACA, 54 to 55 min; and 3kPZ, 58 to 59 min.

Separation of 3kPZS and 3kACA

Diethyl ether extraction of water at pH 4 removed the immunoactivity in fractions 54 to 55 (FIGS. 16B and 16C).

Comparison of Different Life History Stages

Figure 17:
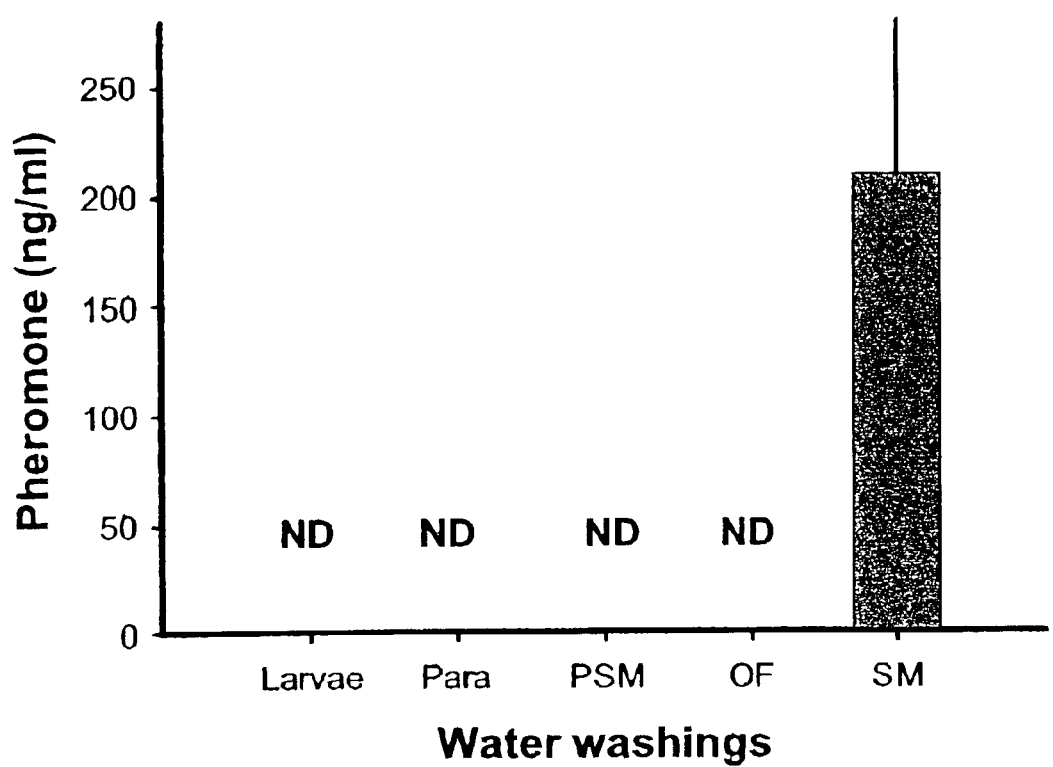
FIG. 17 shows the amounts of 3kPZS-immunoactive material in water (ng/mL SEM) which had been conditioned for 4 hours by larvae (Larvae), parasitic adults (Para), ovulating females (OF), pre-spermiating males (PSM), and spermiating males (SM). There were ten spermiating males and six of each of the other stages. ND=non-detectable (<400 pg/mL).

Water washings from larvae {Larvae), parasites (Para), pre-spermiating males (PSM) and ovulated females (OF) did not contain pheromone at the limits of detection of the assay, which was 400 pg/mL, while the concentration of the pheromone in the samples from 10 spermiating males was on average 209.5 (±70.6, n=10) ng/mL (FIG. 17). The range was 21.5 ng/mL to 7852 ng/mL. The proportion of immunoactivity which could be extracted with diethyl ether from these same water samples (after adjusting them to pH 4) varied between 0.2 and 11.5%, with a mean of 3.0% (±1.1%).

Confirming the Route of Release of the Pheromone

Figure 18:
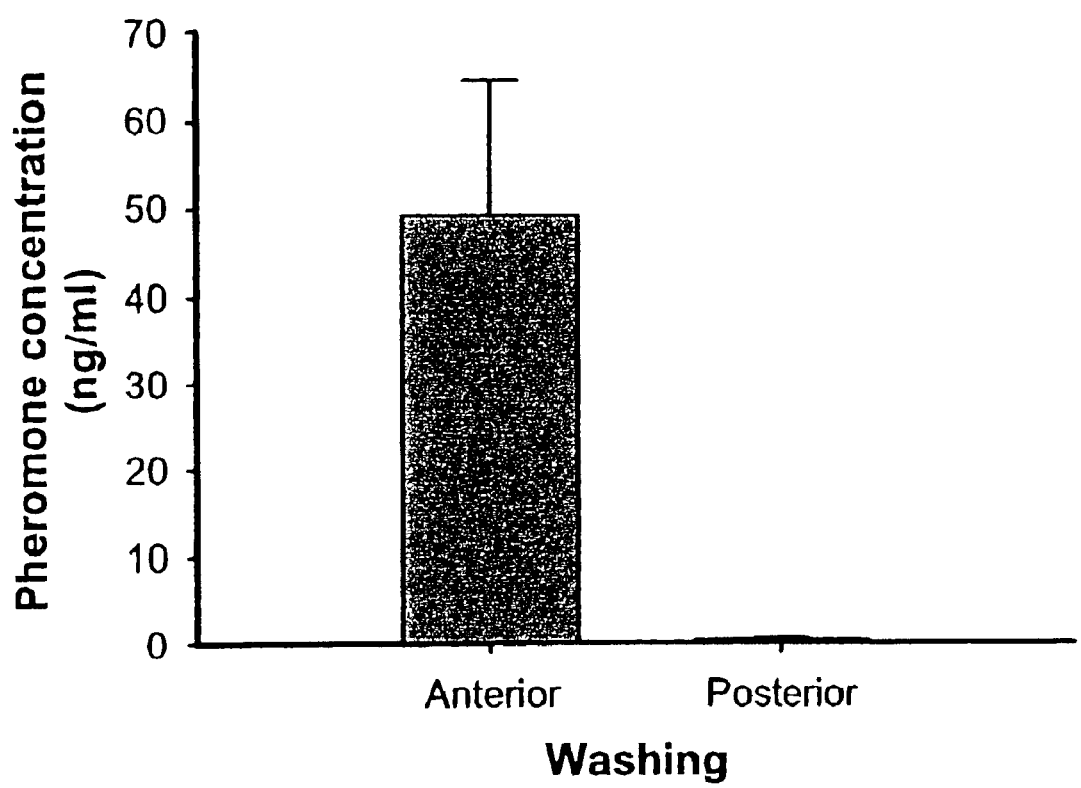
FIG. 18 shows the concentration of 3kPZS immunoactivity (ng/mL) in water from either the head or tail regions of spermiated males (n=5). Total volume of water on each side of the bisected tank was 10 L.

In all five "bisected" males, >99% of immunoactivity was found in the water bathing the head region (FIG. 18). The concentration of the pheromone in the washings from the head region ranged between 2.9 and 113.1 ng/mL, with a mean of 49.0 (±15.5) ng/mL. The concentrations in the water bathing the tail region ranged from undetectable to 1.3 ng/mL.

Discussion

An ELISA has been developed for and successfully applied to the measurement of amounts of pheromone released by captive male lampreys. The standard curve covers a range of 42 fmol to 21 pmol/well and is more sensitive than several previously described RIAs for bile acids with detection limits of 500 fmol to 10 pmol (Davidson et al., J. Clin. Pathol. 33: 390–394 (1980); Hashimoto et al., J. Immunoassay 11: 355–372 (1990); Matsuoka and Okumura, J. Lipid Res. 29, 523–526 (1988); Miller et al., Clin. Chem. 27, 1698–1703 (1981)), but less sensitive than ELISAs and RIAs for steroids (Nash et al., Fish Physiol. Biochem. 22, 355–363 (2000); Cuisset et al., Comp. Biochem. Physiol. L08C, 229–241 (1994)). Sensitivity, however, does not appear to be of crucial importance—in view of the large amounts of 3kPZS that are released into the water by spermiating male lampreys.

The coupling of 3-keto-petromyzonol-24-hemisuccinate to BSA appears to have been successful in producing a relatively specific antiserum. Although, it cross-reacts equally well with 3kPZ and 3kACA, the former was not found in the extracts and the latter can be easily removed by solvent extraction. Although the antiserum appeared to cross-react slightly with the migratory pheromone PZS (1.6%), this was found to be due to contamination. The fact that 3kACA cross-reacts with the antiserum, while ACA does not, highlights the importance of the 3-keto configuration for cross-reactivity.

The assay was validated by checking intra- and inter-assay variation and parallelism of the 3kPZS standard with water which had been conditioned by a spermiating male lamprey. Intra- and inter-assay variances were analyzed according to the procedures of Nash et al., Fish Physiol. Biochem. 22, 355–363 (2000) and were well within the ranges described for other bile acid RIAs (Davidson et al., J. Clin. Pathol. 33, 390–394 (1980); Hashimoto et al., J. Immunoassay 11: 355–372 (1990); Matsuoka and Okwnura, J. Lipid Res. 29: 523–526 (1988); Miller et al., Clin. Chem. 27: 1698–1703 (1981)) and ELISAs (Baqir et al., Anal. Biochem. 93: 361–365 (1979); Ozaki et al., Lipid Res. 20: 240–245 (1979)). Close parallelism of water washings was noted with standard 3kPZS—indicating the reliability of the assay in measuring the pheromone in the water samples.

On HPLC, the fractions with a retention time of 39 to 41 minutes were found to contain most of the immunoactivity, with only one other minor peak, in fractions 54 to 55, being found. These two peaks correspond in elution position, and in relative amounts, to the two peaks of EOG activity, and to two out of three of the bands which could be stained by phosphomolybdic acid on Thin Layer Chromatograms. The results of the ELISA confirm the findings of Example 1 that the first (i.e., larger) peak is 3kPZS. They also strongly indicate that the second minor peak is 3kACA. The fact that these two compounds are released together by the adult male lamprey has a remarkable parallel with the larval lamprey, which synthesizes a mixture of PZS and ACA (Haslewood and Tokes, Biochem. J. 114: 179–184 (1969)). Since a mixture of PZS and ACA appears to be a more potent pheromonal signal for adult lampreys than PZS by itself (Bjerselius et al., Can. J. Fish Aquat. Sci. 57: 557–569 (2000)), then possibly a mixture of 3kPZS and 3kACA is a more potent signal for ovulated females. This remains to be established.

The fact that 3kPZS and 3kACA can be easily separated prior to assay means that both compounds can be separately quantified in water samples. The concentrations of pheromone in the 10 water washings collected from spermiating male lampreys varied from 21.5 to 785.2 ng/mL (or 53.7 µg to 1.9 mg/fish/h) whereas no activity was found in water washings from larval lamprey, parasites, pre-spermiating males, and ovulating females. This confirms the results of Example 1 wherein it was found that only mature males produce 3kPZS at an estimated rate of 250 µg/fish/h—based on the weight of dried pheromone obtained from 10 L of conditioned water.

In an experiment using a bisected aquarium, most of the immunoactivity (>99%) released by spermiating males was found in the washings from the head region, while negligible amounts were found in the washings from the tail region. This supports the results in Example 1—which showed that only water from the head region was able to attract ovulated females. The point source of the pheromone is almost certainly the gills, which in spermiating males contain unique glandular cells (Pickering, Cell Tiss. Res. 180: 1–10 (1977)). It is not yet known whether these are responsible for de novo synthesis of 3kPZS or whether they act as a "pumping station" for 3kPZS which has been made in the liver. With the development of an ELISA, we now have a useful tool for unraveling its mechanism of synthesis and release; and also for determining whether its synthesis is under any sort of hormonal control. One other possible application for the ELISA is to estimate the numbers of male lampreys on a spawning ground—by measuring the amount of 3kPZS in the river water.

In summary, we report an ELISA for 3kPZS which has been validated in a variety of ways. The assay is highly specific—apart from a small amount of cross-reacting material which has been identified as 3kACA and that elutes after 3kPZS on the HPLC. However, this can be removed by prior extraction of the water samples with an organic solvent. The assay was successfully used not only to show how much pheromone is released by sea lampreys in the laboratory but also to show that it is released only from the head region of spermiating males. The ELISA will undoubtedly provide a useful tool for investigating the physiological, ecological, and behavioral aspects of chemical communication in sea lamprey.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A method for attracting a female lamprey in water which comprises:

introducing a composition consisting of 7α,12α,24-trihydroxy-5α-cholan-3-one-24-sulfate and optionally 7α,12α-dihydroxy-5α-cholan-3-one-24-oic acid into the water containing the female lamprey wherein the composition attracts the female lamprey to the region of the water where the composition was introduced.

2. The method of claim 1 wherein the female lamprey is attracted to a trap in the water or a region of the water for sustaining the lampreys.

3. The method of claim 1 wherein the water is a stream in the environment.

4. The method of claim 1 wherein the female lamphrey is in lakes, rivers or streams.

5. The method of claim 1 wherein the female lamphrey is an ovulating female.

* * * * *

UNITED STATES PATENT AND TRADEMARK OFFICE
CERTIFICATE OF CORRECTION

PATENT NO. : 6,881,729 B2
DATED : April 19, 2005
INVENTOR(S) : W. Li et al.

It is certified that error appears in the above-identified patent and that said Letters Patent is hereby corrected as shown below:

Column 5,
Line 34, "regent" should be -- reagent --.

Column 7,
Line 23, "shows a UW" should be -- shows a UV --.

Column 28,
Line 27, "range of 20 g to 10" should be -- range of 20 pg to 10 --.

Column 32,
Line 39, "24-oic acid into" should be -- 24-oic acid as the active ingredient into --.
Lines 48 and 50, "lamphrey" should be -- lamprey --.

Signed and Sealed this

Thirteenth Day of September, 2005

JON W. DUDAS
*Director of the United States Patent and Trademark Office*